United States Patent
Maloney et al.

(10) Patent No.: US 11,173,246 B2
(45) Date of Patent: Nov. 16, 2021

(54) MULTI-COMPONENT INJECTION SYSTEM AND METHODS FOR TISSUE REPAIR

(71) Applicant: ISTO TECHNOLOGIES, INC., St. Louis, MO (US)

(72) Inventors: Michael Maloney, St. Louis, MO (US); Torrey Munger, St. Louis, MO (US); Gary Gage, St. Louis, MO (US); H. Davis Adkisson, IV, St. Louis, MO (US)

(73) Assignee: Isto Technologies, Inc., St. Louis, MO (US)

( * ) Notice: Subject to any disclaimer, the term of this patent is extended or adjusted under 35 U.S.C. 154(b) by 40 days.

(21) Appl. No.: 16/254,404

(22) Filed: Jan. 22, 2019

(65) Prior Publication Data
US 2019/0151546 A1 May 23, 2019

Related U.S. Application Data

(63) Continuation-in-part of application No. PCT/US2017/043522, filed on Jul. 24, 2017.
(Continued)

(51) Int. Cl.
*A61M 5/19* (2006.01)
*A61M 5/31* (2006.01)
(Continued)

(52) U.S. Cl.
CPC .............. *A61M 5/19* (2013.01); *A61M 5/284* (2013.01); *A61M 5/31* (2013.01); *A61M 5/31596* (2013.01); *A61M 5/3286* (2013.01); *A61M 5/16854* (2013.01); *A61M 5/486* (2013.01); *A61M 2005/3114* (2013.01); *A61M 2005/3128* (2013.01); *A61M 2202/07* (2013.01); *A61M 2202/09* (2013.01); *A61M 2205/0294* (2013.01);
(Continued)

(58) Field of Classification Search
CPC .......... A61M 5/19; A61M 5/284; A61M 5/31; A61M 5/31596; A61M 5/3286; A61M 5/486; A61M 2205/502; A61M 5/16854; A61M 2205/3331; A61M 2202/07; A61M 2005/3128; A61M 2205/332; A61M 2205/0294; A61M 2202/09; A61M 2005/3114
USPC .......................................................... 141/18
See application file for complete search history.

(56) References Cited

U.S. PATENT DOCUMENTS 3,957,082 A * 5/1976 Fuson .................. A61M 39/223
137/625.41
4,359,049 A * 11/1982 Redl ................ A61B 17/00491
604/191
(Continued)

FOREIGN PATENT DOCUMENTS

WO 2018/018042 A1 1/2018

OTHER PUBLICATIONS

International Search Report and Written Opinion from related International Application No. PCT/US2017/43522, dated Nov. 17, 2017; 16 pgs.

*Primary Examiner* — Timothy L Maust
*Assistant Examiner* — James R Hakomaki
(74) *Attorney, Agent, or Firm* — Polsinelli PC

(57) ABSTRACT

The present disclosure provides devices, kits and methods for preparing injections with cells and carrier components
(Continued)

for delivery to a target area in the body. The disclosed devices, kits, and methods provide preparation and monitoring of injections.

15 Claims, 7 Drawing Sheets

Related U.S. Application Data

(60) Provisional application No. 62/365,688, filed on Jul. 22, 2016.

(51) Int. Cl.
*A61M 5/315* (2006.01)
*A61M 5/32* (2006.01)
*A61M 5/28* (2006.01)
*A61M 5/48* (2006.01)
*A61M 5/168* (2006.01)

(52) U.S. Cl.
CPC ............ *A61M 2205/332* (2013.01); *A61M 2205/3331* (2013.01); *A61M 2205/502* (2013.01)

(56) References Cited

U.S. PATENT DOCUMENTS

| | | | | |
|---|---|---|---|---|
| 4,619,643 A * | 10/1986 | Bai | ............... | A61M 5/1582 604/170.03 |
| 5,104,375 A * | 4/1992 | Wolf | ............... | A61B 17/00491 206/364 |
| 5,116,315 A * | 5/1992 | Capozzi | ............... | A61B 17/00491 222/137 |
| 5,236,417 A * | 8/1993 | Wallis | ............... | A61M 25/00 600/432 |
| 5,290,259 A * | 3/1994 | Fischer | ............... | A61M 5/19 222/137 |
| 5,449,344 A * | 9/1995 | Taylor | ............... | A61M 25/10182 604/100.03 |
| 5,480,380 A * | 1/1996 | Martin | ............... | A61M 5/1582 604/284 |
| 5,988,230 A * | 11/1999 | Black | ............... | A61C 9/0026 141/18 |
| 6,113,571 A * | 9/2000 | Zinger | ............... | A61B 17/00491 604/191 |
| 7,037,289 B2 * | 5/2006 | Dodge | ............... | A61B 17/00491 604/191 |
| 7,270,648 B2 * | 9/2007 | Kazemzadeh | ............... | A61M 5/1454 604/135 |
| 7,322,956 B2 * | 1/2008 | Fehr | ............... | A61M 5/19 604/82 |
| D589,142 S * | 3/2009 | Guerrero | ............... | D24/108 |
| 7,635,343 B2 * | 12/2009 | McIntosh | ............... | A61B 17/00491 604/82 |
| 7,785,312 B2 * | 8/2010 | Thorne, Jr. | ............... | A61M 39/16 604/500 |
| 7,883,501 B2 * | 2/2011 | McIntosh | ............... | A61C 5/64 604/506 |
| 8,052,421 B2 * | 11/2011 | Pierson | ............... | B05C 17/00516 433/90 |
| 8,118,776 B2 * | 2/2012 | Lampropoulos | ............... | A61M 25/1018 604/97.03 |
| 8,403,882 B2 * | 3/2013 | Goldberg | ............... | A61B 17/00491 604/82 |
| 8,684,964 B2 * | 4/2014 | Stevens | ............... | A61M 25/10188 604/99.01 |
| 8,753,670 B2 * | 6/2014 | Delmotte | ............... | A61L 15/44 424/443 |
| 9,107,668 B2 * | 8/2015 | Melsheimer | ............... | A61B 17/12109 |
| 9,861,756 B1 * | 1/2018 | Krasnow | ............... | G01F 11/027 |
| 10,166,514 B2 * | 1/2019 | Delmotte | ............... | B01F 11/0071 |
| 2001/0016709 A1 | 8/2001 | Tovey et al. | | |
| 2002/0117232 A1 * | 8/2002 | Gisper-Sauch | ............... | B65B 3/003 141/2 |
| 2003/0181850 A1 | 9/2003 | Diamond et al. | | |
| 2006/0089604 A1 * | 4/2006 | Guerrero | ............... | A61M 5/1408 604/247 |
| 2007/0213660 A1 | 9/2007 | Richards et al. | | |
| 2008/0161772 A1 | 7/2008 | Nayak et al. | | |
| 2008/0243049 A1 * | 10/2008 | Hardy | ............... | A61K 9/0009 604/22 |
| 2008/0294089 A1 * | 11/2008 | Hardy | ............... | A61K 47/6911 604/22 |
| 2009/0118696 A1 | 5/2009 | Nyhart, Jr. | | |
| 2011/0033925 A1 | 2/2011 | Duffy, Jr. et al. | | |
| 2011/0202012 A1 * | 8/2011 | Bartlett | ............... | A61M 5/3287 604/218 |
| 2011/0270027 A1 * | 11/2011 | Augarten | ............... | A61M 5/486 600/37 |
| 2013/0172823 A1 * | 7/2013 | Meron | ............... | A61B 17/00491 604/205 |
| 2014/0081208 A1 | 3/2014 | Maloney | | |
| 2014/0088712 A1 * | 3/2014 | Gage | ............... | A61B 17/8816 623/17.16 |
| 2014/0288408 A1 * | 9/2014 | Deutsch | ............... | A61M 5/31511 600/407 |
| 2015/0262512 A1 | 9/2015 | Rios et al. | | |
| 2015/0329875 A1 * | 11/2015 | Gregory | ............... | C12N 9/22 435/462 |
| 2016/0101213 A1 * | 4/2016 | Seyedin | ............... | A61L 27/3817 424/486 |
| 2016/0259913 A1 * | 9/2016 | Yu | ............... | G16H 20/17 |
| 2017/0136185 A1 * | 5/2017 | Rios | ............... | A61M 5/31511 |
| 2017/0312430 A1 * | 11/2017 | Schleicher | ............... | A61M 5/1723 |

* cited by examiner

MULTI-COMPONENT INJECTION SYSTEM AND METHODS FOR TISSUE REPAIR

CROSS REFERENCE TO RELATED APPLICATIONS

This application is a continuation-in-part of PCT Patent Application No. PCT/US2017/043522 entitled "MULTI-COMPONENT INJECTION SYSTEM AND METHODS FOR TISSUE REPAIR" filed Jul. 24, 2017, the entire disclosure of which is incorporated herein by reference and claims priority to U.S. Provisional Patent Application 62/365,688, entitled "MULTI-COMPONENT INJECTION SYSTEM AND METHODS FOR TISSUE REPAIR" filed on Jul. 22, 2016, which is also hereby incorporated by reference in its entirety.

FIELD OF THE INVENTION

The present disclosure relates generally to medical injection devices, methods and kits, and in particular to medical injection devices for preparing an injection of a multi-component composition for repair of a tissue defect.

BACKGROUND OF THE INVENTION

Recent advances in cell-based medical therapies include the development of an injectable, cell-based fluid composition that can be injected into damaged or diseased tissue to repair the tissue. For example, an injectable cell-based fluid composition can be used for resolving back pain associated with degenerative disease of the intervertebral disc. The treatment involves the combination of two components in a single fluid stream for injection directly into the disc, via a spinal injection needle placed in the target intervertebral disc. However, the injection components may need to remain separate until reaching the target, so that the components polymerize within the target and not while injecting the components. Therefore, there is a need for preparing an injection but keeping the injection components separate.

Furthermore, the cells may be within a cryovial that is not sterile on the outside, but the cells on the inside must remain sterile. Devices and methods for preparing and delivering cells from a cryovial to a fully sterile delivery area and mixing the cells with the injection components, while maintaining the separation of the components, are therefore needed.

Additionally, the injection pressure at the needle-tip can, if excessive, cause further damage to already compromised tissue. To avoid further damage to already compromised tissue, injection pressure must somehow be monitored and controlled. Various approaches to doing so are theoretically possible, but pressure cut-offs are not clear, and certain monitoring/control approaches can further complicate treatment by reducing the accuracy of fluid delivery to the tissue. Devices and methods for monitoring and controlling injection pressure for injection of a therapeutic fluid composition are therefore needed.

SUMMARY OF THE INVENTION

In one aspect, the present disclosure provides an injection preparation device including a body to reversibly engage a multi-barrel carrier syringe, a cell delivery syringe and a carrier delivery syringe. The body may include a first transfer portion defining a first inlet to reversibly couple to a first barrel of the multi-barrel carrier syringe, and a second inlet to reversibly couple to the barrel of the cell delivery syringe, and a second transfer portion defining a third inlet configured to reversibly couple to a second barrel of the multi-barrel carrier syringe, and a fourth inlet to reversibly couple to the barrel of the carrier delivery syringe. The first inlet and second inlet communicate through a first conduit through the body, and the third and fourth inlets communicate through a second conduit through the body. The body, such as the first inlet, may reversibly couple to a cell transfer syringe. At least one of the first, second, third, and fourth inlets includes a female connector port projecting from the body, where each female connector port may receive the injection end of a barrel of the carrier syringe or the delivery syringe. At least one of the first, second, third, and fourth inlets includes a male connector port projecting from the body, where each male connector port may reversibly engage a female connector coupled to a barrel of the carrier syringe or the delivery syringe. At least one of the first, second, third, and fourth inlets may include a luer connector.

In another aspect, the present disclosure provides an injection preparation kit including the injection preparation described herein above, and at least one of a multi-barrel carrier syringe, a cell transfer syringe, a cell delivery syringe and a carrier delivery syringe. At least one or more of the multi-barrel carrier syringe, cell transfer syringe, cell delivery syringe and carrier delivery syringe may be coupled to the body. The multi-barrel carrier syringe, cell delivery syringe and carrier delivery syringe may be coupled to the body. The carrier syringe may include two barrels and a double-barrel plunger rod assembly to transfer a first predetermined amount of a first carrier component and a second predetermined amount of a second carrier component. The kit may include the cell delivery syringe and the carrier delivery syringe or the cell transfer syringe. In one aspect, the cell transfer syringe may be a single-barrel syringe.

In another aspect, the present disclosure provides an injection preparation device including a body adapted to reversibly couple to a multi-barrel carrier syringe and a multi-barrel delivery syringe, the body having a first transfer portion defining a first inlet configured to reversibly couple to a first barrel of the multi-barrel carrier syringe and a second inlet configured to reversibly couple to a first barrel of the multi-barrel delivery syringe, and a second transfer portion defining a third inlet configured to reversibly couple to a second barrel of the multi-barrel carrier syringe, and a fourth inlet configured to reversibly couple to a second barrel of the multi-barrel delivery syringe. The first inlet and second inlet communicate through a first conduit through the body, and the third and fourth inlets communicate through a second conduit through the body. The body may reversibly couple to a cell transfer syringe, for example, the first inlet may reversibly couple to the cell transfer syringe. At least one of the first, second, third and fourth inlets includes a female connector port projecting from the body, where each female connector port may receive the injection end of a barrel of one of the carrier or delivery syringes. At least one of the first, second, third, and fourth inlets includes a male connector port projecting from the body, each male connector port may reversibly engage a female connector coupled to a barrel of the carrier syringe or the delivery syringe. At least one of the first, second, third and fourth inlets may include a luer connector.

In another aspect, the present disclosure provides an injection preparation kit including the injection preparation device described herein above, and at least one of the multi-barrel carrier syringe, the multi-barrel delivery syringe and the cell transfer syringe. At least one or more of the multi-barrel carrier syringe, the multi-barrel delivery syringe and the cell transfer syringe may be coupled to the body. In one aspect, the multi-barrel carrier syringe and the multi-barrel delivery syringe may be coupled to the body. In another aspect, the multi-barrel delivery syringe and the cell transfer syringe may be coupled to the body. The multi-barrel delivery syringe may include two barrels and a double-barrel plunger rod assembly. The kit may include the multi-barrel delivery syringe or the cell transfer syringe. The cell transfer syringe may be a single-barrel syringe.

In another aspect, the present disclosure provides an injection preparation device including a body to reversibly engage a multi-barrel carrier syringe, a cell transfer syringe, a cell delivery syringe and a carrier delivery syringe, the body including a first transfer portion defining a first inlet to reversibly couple to a first barrel of the multi-barrel carrier syringe, a second inlet to reversibly couple to the barrel of the cell delivery syringe, and a fifth inlet to reversibly couple to the barrel of the cell transfer syringe, and a second transfer portion defining a third inlet to reversibly couple to a second barrel of the multi-barrel carrier syringe, and a fourth inlet to reversibly couple to the barrel of the carrier delivery syringe. The first, second, and fifth inlets communicate through a first conduit through the body, and the third and fourth inlets communicate through a second conduit through the body. At least one of the first, second, third, fourth and fifth inlets may include a female connector port projecting from the body, where each female connector port may receive the injection end of a barrel of the carrier syringe or the delivery syringe. At least one of the first, second, third, fourth and fifth inlets may include a male connector port projecting from the body, where each male connector port may reversibly engage a female connector coupled to a barrel of the carrier syringe or the delivery syringe. At least one of the first, second, third, fourth and fifth inlets may include a luer connector. The first transfer portion may include a two-way valve to limit a fluid path between the first and second inlets or between the first and fifth inlets. The third inlet defined by the second transfer portion may include a one-way valve.

In another aspect, the present disclosure provides an injection preparation kit including the injection preparation device described herein above, and at least one of a multi-barrel carrier syringe, a cell transfer syringe, a cell delivery syringe and a carrier delivery syringe. At least one or more of the multi-barrel carrier syringe, cell transfer syringe, cell delivery syringe and carrier delivery syringe may be coupled to the body. The multi-barrel carrier syringe, cell delivery syringe and carrier delivery syringe may be coupled to the body. The injection preparation kit may include the multi-barrel carrier syringe. The injection preparation kit may include the multi-barrel delivery syringe, where the delivery syringe includes two barrels and a double-barrel plunger rod assembly. The injection preparation kit may include the cell transfer syringe. The cell transfer syringe may be a single-barrel syringe.

In another aspect, the present disclosure provides an injection preparation device including a body adapted to reversibly couple to a multi-barrel carrier syringe, a multi-barrel delivery syringe and a cell transfer syringe, the body having a first transfer portion defining a first inlet to reversibly couple to a first barrel of the multi-barrel carrier syringe, a second inlet to reversibly couple to a first barrel of the multi-barrel delivery syringe, and a fifth inlet to reversibly couple to the cell transfer syringe, and a second transfer portion defining a third inlet configured to reversibly couple to a second barrel of the multi-barrel carrier syringe, and a fourth inlet configured to reversibly couple to a second barrel of the multi-barrel delivery syringe. The first inlet, second inlet and fifth inlet communicate through a first conduit through the body, and the third and fourth inlets communicate through a second conduit through the body. At least one of the first, second, third, fourth and fifth inlets may include a female connector port projecting from the body, where each female connector port may receive the injection end of a barrel of one of the carrier, delivery or cell transfer syringes. At least one of the first, second, third, fourth and fifth inlets may include a male connector port projecting from the body, each male connector port may reversibly engage a female connector coupled to a barrel of the carrier syringe or the delivery syringe. At least one of the first, second, third, fourth and fifth inlets may be a luer connector. The first transfer portion may include a two-way valve to limit a fluid path between the first and second inlets or between the first and fifth inlets. The second inlet defined by the second transfer portion may include a one-way valve.

In another aspect, the present disclosure provides an injection preparation kit including the injection preparation device described herein above and at least one of the multi-barrel carrier syringe, the multi-barrel delivery syringe and the cell transfer syringe. At least one or more of the multi-barrel carrier syringe, the multi-barrel delivery syringe and the cell transfer syringe may be coupled to the body. The multi-barrel carrier syringe and the multi-barrel delivery syringe may be coupled to the body. The injection preparation kit includes the multi-barrel delivery syringe, where the delivery syringe includes two barrels and a double-barrel plunger rod assembly. The injection preparation kit includes the cell transfer syringe. The cell transfer syringe may be a single-barrel syringe.

In another aspect, the present disclosure provides a cell transfer container for use with a cell storage container having an opening covered by a sterile seal capable of penetration by a hollow needle. The cell transfer container may include a body having a first surface and a second surface and define an opening therethrough from the first surface to the second surface, the opening having a rim; a substantially tubular projection from the first surface defining a wall surrounding the opening; and the hollow needle disposed perpendicular to the first surface from within the wall. The hollow needle may be coupled to the rim of the opening and the hollow needle may have a length less than or equal to a depth of the tubular projection from the first surface. The body may be substantially planar. The cell transfer container may include a connector port projecting from the body second surface, where the connector port defines a wall surrounding the opening and where the connector port may engage a syringe barrel. The connector port may include a female luer port to reversibly engage a male luer-tipped syringe. The wall of the substantially tubular projection may define an opening therethrough so that the contents of the cell storage container may be visible when the cell transfer container is in use to penetrate the seal by contacting the seal with the hollow needle. The cell transfer container may include a removable adhesive sterile barrier disposed over the opening through the body.

In another aspect, the present disclosure provides an injection preparation kit for transferring a prepared cell composition from a cell storage container to a cell transfer syringe. The kit may include at least one of the injection preparation devices described herein above and the cell transfer container. The injection preparation kit may include a cell storage container including a substantially cylindrical body defining a central lumen, a first end and a second end, wherein the first end defines a vent port and a fill port, and the second end defines an access port, and a flexible sealing element over the access port, wherein the vent port, fill port and access port communicate with the central lumen. The injection preparation kit may include a cell storage container including a substantially cylindrical body defining a central lumen, a first end and a second end, where the first end defines a fill opening, and the second end defines an access port and a flexible sealing element over the access port; and a cap configured to seal the fill opening, where the fill opening and access port communicate with the central lumen. The flexible sealing element may include a rubber septum. The cell storage container has an inner surface and an outer surface, where the inner surface may be sterile and the outer surface may be non-sterile. The cell storage container contains a prepared cell composition for transfer to a delivery syringe. The second end may further define a connector port for reversibly engaging a connector port of a second device. The cell storage container may operate with an automated filling machine.

The injection preparation kit may further include an amount of the prepared cell composition. The injection preparation kit may further include an amount of at least a first carrier component. The injection preparation kit may further include an amount of a second carrier component, where the amounts of the first and the second carrier components are packaged separately. The first and the second carrier components when combined form a polymerized hydrogel.

In another aspect, the present disclosure provides a combination of at least one of any one of the injection preparation devices and cell transfer container described herein above in combination with an injection load monitoring device to reversibly couple to a delivery syringe. The injection load monitoring device may include a mechanical load sensor having an amplifier and an electrical coupling coupled thereto for coupling to a pressure display unit; a syringe adapter coupled to the mechanical load sensor, the syringe adapter having a first surface configured to engage an outward end portion of a plunger rod of a plunger rod assembly of the delivery syringe; and a finger plate coupled to the mechanical load sensor. The mechanical load sensor may be selected from a miniature or subminiature load cell and a piezoresistive mechanical load sensor. The mechanical load sensor may be operable for measuring a compression load of up to about 100 lb. The mechanical load display unit displays a visual alarm, an auditory alarm, or both in response to the mechanical load applied to the delivery syringe. The mechanical load display unit may be directly coupled to the syringe adapter or finger plate. The pressure display unit is configured for wireless communication with the mechanical load sensor.

The injection preparation kit may further include a Y-connector to reversibly couple to a multi-barrel delivery syringe. The Y-connector includes a connector body having a first end and a second end, the first end defining at least two connector inlets for reversibly coupling the Y-connector to the at least two barrels of the delivery syringe; a dual lumen cannula coupled to the second end of the connector body; and a spinal needle coupled to the dual lumen cannula. In an aspect, the injection preparation kit may further include a light source or light conduit. The light source may be used to expose a photoactivated polymer(s) at or near the end of the cannula. In various aspects, the light source and/or light conduit may be associated with the Y-connector, spinal needle, or delivery syringe.

In another aspect, the present disclosure provides any combination described herein further including an amount of at least a first carrier component, the combination further including an amount of a second carrier component, where the amounts of the first and the second carrier components are packaged separately. The first and the second carrier components when combined form a polymerized hydrogel.

In another aspect, the present disclosure provides a method of preparing a multi-component injection, including obtaining a carrier syringe including at least two barrels with a first carrier component in a first barrel and a second carrier component in a second barrel; coupling a first barrel of the carrier syringe to the first inlet of an injection preparation device, and a second barrel of the carrier syringe to the third inlet of the injection preparation device; coupling a cell delivery syringe to the second inlet of the injection preparation device; coupling a carrier delivery syringe to the fourth inlet of the injection preparation device; and transferring the first carrier component from the first barrel of the carrier syringe to the cell delivery syringe through the first conduit of the injection preparation device; and transferring the second carrier component from the second barrel of the carrier syringe to the carrier delivery syringe through the second conduit of the injection preparation device, where dual plunger rod assembly used with the carrier syringe may be configured to transfer a predetermined amount of the first carrier component to the cell delivery syringe and a predetermined amount of the second carrier component to the carrier delivery syringe. The method may further include coupling a cell transfer syringe to the injection preparation device. The cell transfer syringe may be coupled to the first inlet of the injection preparation device. The method may further include: removing the carrier syringe from the injection preparation device; coupling a cell transfer syringe to the injection preparation device, where the cell transfer syringe contains a cell composition; transferring the first carrier component from the cell delivery syringe to the cell transfer syringe though the first conduit, whereby the first carrier component is mixed with the cell composition to form a first cell/carrier mixture; and transferring the first cell/carrier mixture back to the cell delivery syringe through the first conduit.

In another aspect, the present disclosure provides a method of preparing a multi-component injection, including: filling a carrier syringe including at least two barrels with a first carrier component in a first barrel and a second carrier component in a second barrel; coupling the two barrels of the carrier syringe to the first and third inlets of an injection preparation device, coupling the two barrels of the delivery syringe to the second and fourth inlets of the injection preparation device, and transferring the first carrier component from the first barrel of the carrier syringe to a first barrel of the delivery syringe through the first conduit of the injection preparation device, and the second carrier component from the second barrel of the carrier syringe to a second barrel of the delivery syringe through the second conduit of the injection preparation device, where a plunger used with the carrier syringe may be configured to transfer a predetermined amount of the first carrier component and a predetermined amount of the second carrier component to the delivery syringe. The method further including: removing the carrier syringe from the injection preparation device; coupling a cell transfer syringe to the injection preparation device, where the cell transfer syringe contains a cell composition; transferring the first carrier component from the first barrel of the delivery syringe to the cell transfer syringe though the first conduit, whereby the first carrier component is mixed with the cell composition to form a first cell/carrier mixture; and transferring the first cell/carrier mixture back to the first barrel of the delivery syringe through the first conduit. The cell transfer syringe may be coupled to the first inlet of the injection preparation device. The method may further include decoupling the delivery syringe from the injection preparation device, where the first barrel of the delivery syringe contains the first cell/carrier mixture and the second barrel of the delivery syringe contains the second carrier component.

In another aspect, the present disclosure provides a method of preparing a multi-component injection, including: obtaining a carrier syringe including at least two barrels with a first carrier component in a first barrel and a second carrier component in a second barrel; coupling a first barrel of the carrier syringe to the first inlet of the injection preparation device, and a second barrel of the carrier syringe to the third inlet of the injection preparation device; coupling a cell delivery syringe to the second inlet of the injection preparation device; coupling a cell transfer syringe to the fifth inlet of the injection preparation device; coupling a carrier delivery syringe to the fourth inlet of the injection preparation device; and transferring the second carrier component from the second barrel of the carrier syringe to the carrier delivery syringe through the second conduit of the injection preparation device; limiting the flow path through the first conduit of the injection preparation device to between the first inlet and the fifth inlet, and transferring the first carrier component from the first barrel of the carrier syringe to the cell transfer syringe through the first conduit of the injection preparation device, where a dual plunger rod assembly used with the carrier syringe is configured to transfer a predetermined amount of the first carrier component to the cell transfer syringe and a predetermined amount of the second carrier component to the delivery syringe, whereby the first carrier component mixes with the contents of the cell transfer syringe; and limiting the flow path through the first conduit of the injection preparation device to between the fifth inlet and the second inlet, and transferring the mixture in the cell transfer syringe to the cell delivery syringe. The method further including decoupling the cell delivery syringe and the carrier delivery syringe from the injection preparation device, where the carrier delivery syringe contains the second carrier component and the cell delivery syringe contains a first cell/carrier mixture.

In another aspect, the present disclosure provides a method of preparing a multi-component injection, including: filling a carrier syringe including at least two barrels with a first carrier component in a first barrel and a second carrier component in a second barrel; coupling the two barrels of the carrier syringe to the first and third inlets of an injection preparation device, coupling the two barrels of the delivery syringe to the second and fourth inlets of the injection preparation device, and transferring the first carrier component from the first barrel of the carrier syringe to a first barrel of the delivery syringe through the first conduit of the injection preparation device, and the second carrier component from the second barrel of the carrier syringe to a second barrel of the delivery syringe through the second conduit of the injection preparation device, where a plunger used with the carrier syringe is configured to transfer a predetermined amount of the first carrier component and a predetermined amount of the second carrier component to the delivery syringe. The method further including: removing the carrier syringe from the injection preparation device; coupling a cell transfer syringe to the injection preparation device, where the cell transfer syringe contains a cell composition; transferring the first carrier component from the first barrel of the delivery syringe to the cell transfer syringe though the first conduit, whereby the first carrier component is mixed with the cell composition to form a first cell/carrier mixture; and transferring the first cell/carrier mixture back to the first barrel of the delivery syringe through the first conduit. The method further including decoupling the delivery syringe from the injection preparation device, where the first barrel of the delivery syringe contains the first cell/carrier mixture and the second barrel of the delivery syringe contains the second carrier component.

In any of the methods described herein, the method may further include coupling the delivery syringe to a Y-connector having a stem portion, and ejecting the first cell/carrier mixture from the first barrel of the delivery syringe or the cell delivery syringe and the second carrier component from the second barrel of the delivery syringe or the carrier delivery syringe through the Y-connector, whereby the first cell/carrier mixture and the second carrier component are combined in the Y-connector stem portion to form a cell/carrier composition. The method further including injecting the cell/carrier composition into a tissue defect. The tissue may include bone, cartilage or soft tissue. The method may further include injecting the cell/carrier composition into a degenerated intervertebral disc. The Y-connector may be configured to reversibly couple to the cell delivery syringe and to the carrier delivery syringe, and the Y-connector includes a connector body having a first end and a second end, the first end defining at least two connector inlets for reversibly coupling the Y-connector to the cell delivery syringe and the carrier delivery syringe or to the at least two barrels of the delivery syringe; the method further including coupling a dual lumen cannula to the second end of the Y-connector body, and coupling a spinal needle to the dual lumen cannula.

In any of the methods described herein, the method may further include providing a light source or light conduit for exposing a photoactivated polymer(s) at or near the end of the cannula. In various aspects, the light source and/or light conduit may be associated with the Y-connector, spinal needle, or delivery syringe.

In any of the methods described herein, the method may further include monitoring the injection load using an injection load monitoring device reversibly coupled to the cell delivery syringe, the injection load monitoring device including a mechanical load sensor having an amplifier and an electrical coupling coupled thereto for coupling to a pressure display unit; a syringe adapter coupled to the mechanical load sensor, the syringe adapter having a first surface configured to engage an outward end portion of a plunger rod of a plunger rod assembly of the delivery syringe; and a finger plate coupled to the mechanical load sensor. The method may further include monitoring the injection load using an injection load monitoring device reversibly coupled to the delivery syringe, the injection load monitoring device including: a mechanical load sensor having an amplifier and an electrical coupling coupled thereto for coupling to a pressure display unit; a syringe adapter coupled to the mechanical load sensor, the syringe adapter having a first surface configured to engage an outward end portion of a plunger rod of a plunger rod assembly of the delivery syringe; and a finger plate coupled to the mechanical load sensor. The mechanical load sensor is selected from a miniature or subminiature load cell and a piezoresistive force sensor. The mechanical load sensor may be operable for measuring a compression load of up to about 100 lb. The pressure display unit displays a visual alarm, an auditory alarm, or both in response to the pressure applied to the delivery syringe. The pressure display unit may be directly coupled to the syringe adapter or finger plate. The pressure display unit is coupled to the mechanical load sensor wirelessly. The delivery syringe contains a prepared cell composition.

In any of the devices, kits and methods described herein, any combination described herein may include the cell storage container and further include a prepared cell composition. The prepared cell composition may include cells selected from adipocytes, neuronal stem cells, chondrocytes, notochordal cells, chondrogenic cells, mesenchymal stem cells, hematopoietic stem cells, and any pluripotent stem cells, including embryonic and induced pluripotent stem cells. The prepared cell composition may include mesenchymal stem cells derived from at least one of bone marrow, adipose tissue, synovium, periosteum, post-partum connective tissue, placenta, cord blood, and umbilical cord.

In any of the devices, kits and methods described herein, the carrier syringe may include two barrels and a double-barrel plunger rod assembly configured to transfer a first predetermined amount of a first carrier component and a second predetermined amount of a second carrier component. The double-barrel plunger rod assembly may include a first plunger rod for slidably engaging the first barrel of the carrier syringe and a second plunger rod for slidably engaging the second barrel of the carrier syringe, where the first plunger rod is shorter than the second plunger rod so that the first predetermined amount of the first carrier component is less than the second predetermined amount of the second carrier component.

In any of the devices, kits and methods described herein, the first carrier component may be thrombin and the second carrier component may be fibrinogen. The first and/or the second carrier component may include polymers selected from: poly(ethylene glycol) (PEG), poly(ethylene oxide) (PEO), poly(vinyl alcohol) (PVA), PEG-polystyrene copolymers (PEG)-(PST), polylactic acid (PLA), ethylene glycol-lactic acid copolymers, ethylene glycol-lactic acid-caprolactone copolymers, poly(d,l-lactide-co-ε-caprolactone), (poly)-anhydrides, anhydrides, urethanes, polysaccharides, dextran, collagen, hyaluronic acid, diethyl fumarate/poly(propylene fumarate), chitosan, a caprolactone polymer such as polycaprolactone (PCL), polyglycolic acid (PGA), or a copolymer of polylactic acid and polyglycolic acid (PLGA), and combinations thereof. In another aspect, the first carrier component may be a photoactive polymerizing polymer and the first carrier component may further include a photoinitiator. The first predetermined amount may be about 0.5 to about 0.7 cc and the second predetermined amount may be about 1.0 to about 1.2 cc. In one aspect, the first predetermined amount may be about 0.6 cc and the second predetermined amount may be about 1.1 cc.

DETAILED DESCRIPTION OF THE DISCLOSURE

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular.

The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The present disclosure encompasses devices, systems, kits and methods for conveniently and efficiently preparing and then delivering by injection a tissue repair composition comprising multiple components that must be combined prior to the injection. Any such tissue repair composition which is obtained by the combination of multiple components is contemplated. Such tissue repair compositions include but are not limited to cell-based compositions comprising a cell composition combined with at least a carrier, for example a protein or protein-based carrier, and the carrier itself may be comprised of multiple components.

A. Injection Preparation Devices i. 4-Inlet Injection Preparation Device

Figure 1:
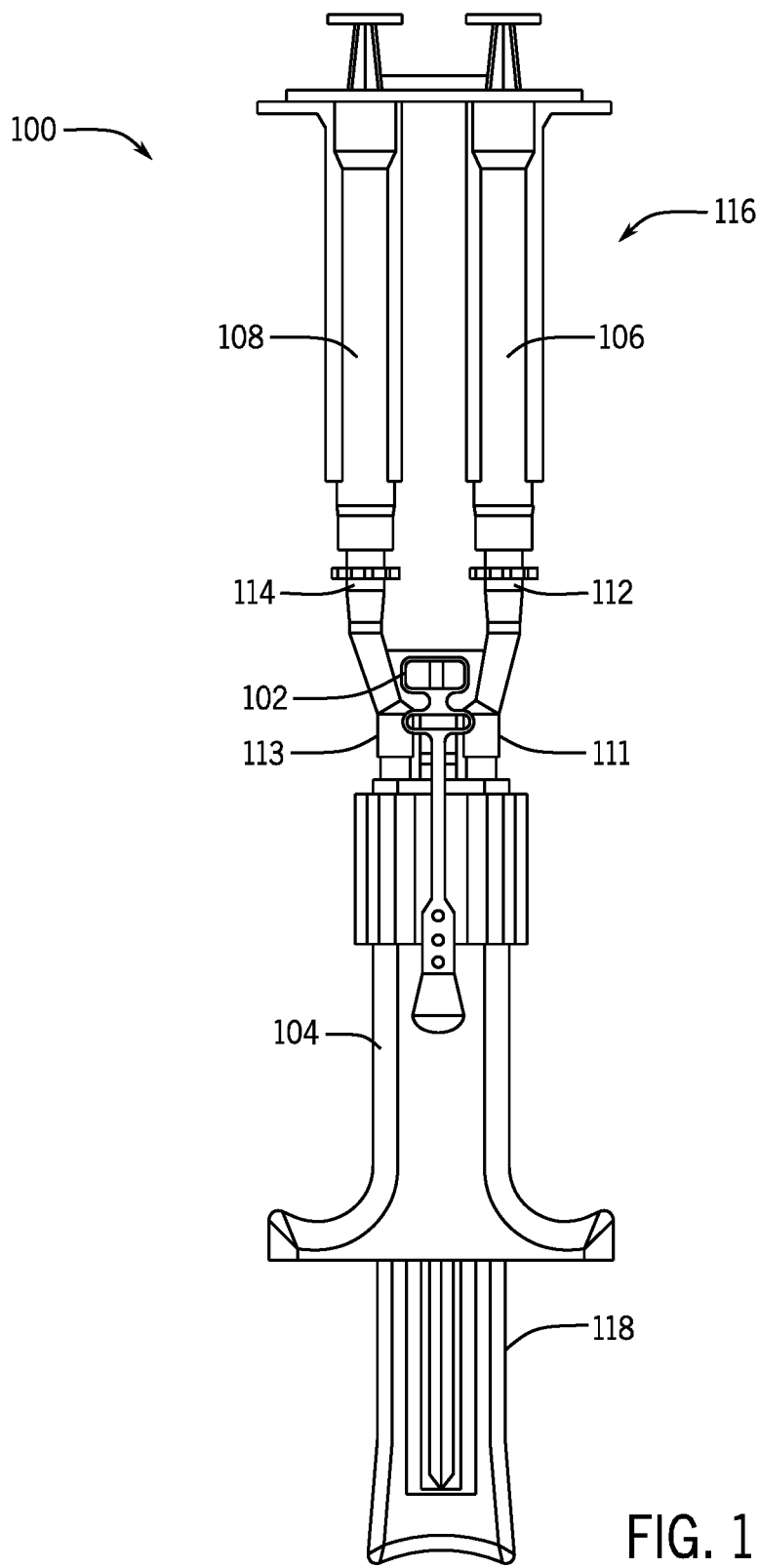
FIG. 1 is a drawing of a four-inlet injection preparation device with a multi-barrel carrier syringe and a multi-barrel delivery syringe.

FIG. 1 is a drawing of an injection preparation device with four inlets 100. In one aspect, the four-inlet injection preparation device 100 includes a body 102 to reversibly engage a multi-barrel carrier syringe 104, a cell delivery syringe 106 and a carrier delivery syringe 108. The body 102 may include a first transfer portion defining a first inlet 111 to reversibly couple to a first barrel of the multi-barrel carrier syringe 104, and a second inlet 112 to reversibly couple to the barrel of the cell delivery syringe 106 and a second transfer portion defining a third inlet 113 configured to reversibly couple to a second barrel of the multi-barrel carrier syringe 104, a fourth inlet 114 to reversibly couple to the barrel of the carrier delivery syringe 108. The first inlet and second inlet communicate through a first conduit through the body 102, and the third and fourth inlets communicate through a second conduit through the body 102. The body 102, for example, the first inlet 111, may reversibly couple to a cell transfer syringe (not shown).

At least one of the first, second, third, and fourth inlets 111-114 may include a female connector port projecting from the body, where each female connector port may receive the injection end of a barrel of the carrier syringe 104 or a delivery syringe 116. At least one of the first, second, third, and fourth inlets 111-114 may include a male connector port projecting from the body, where each male connector port may reversibly engage a female connector coupled to a barrel of the carrier syringe 104 or a delivery syringe 116. In one aspect, at least one of the first, second, third, and fourth inlets 111-114 may include a luer connector.

In another aspect, the present disclosure provides a four-inlet injection preparation device 100, where the cell delivery syringe 106 and the carrier delivery syringe 108 may be multiple barrels of a multi-barrel delivery syringe 116. This aspect may include a body 102 adapted to reversibly couple to a multi-barrel carrier syringe 104 and a multi-barrel delivery syringe 116, the body 102 having a first transfer portion defining a first inlet 111 configured to reversibly couple to a first barrel of the multi-barrel carrier syringe 104 and a second inlet 112 configured to reversibly couple to a first barrel of the multi-barrel delivery syringe 116, and a second transfer portion defining a third inlet 113 configured to reversibly couple to a second barrel of the multi-barrel carrier syringe 104, and a fourth inlet 114 configured to reversibly couple to a second barrel of the multi-barrel delivery syringe 116. The first inlet 111 and second inlet 112 communicate through a first conduit through the body, and the third 113 and fourth inlets 114 communicate through a second conduit through the body. The body 102 may reversibly couple to a cell transfer syringe (not shown). For example, the first inlet 111 may reversibly couple to the cell transfer syringe.

At least one of the first, second, third and fourth inlets 111-114 may include a female connector port projecting from the body 102, where each female connector port may receive the injection end of a barrel of one of the carrier 104 or delivery syringe 116. At least one of the first, second, third, and fourth inlets 111-114 may include a male connector port projecting from the body 102, each male connector port may reversibly engage a female connector coupled to a barrel of the carrier syringe 104 or the delivery syringe 116. In one aspect, at least one of the first, second, third and fourth inlets 111-114 may include a luer connector.

Figure 6:
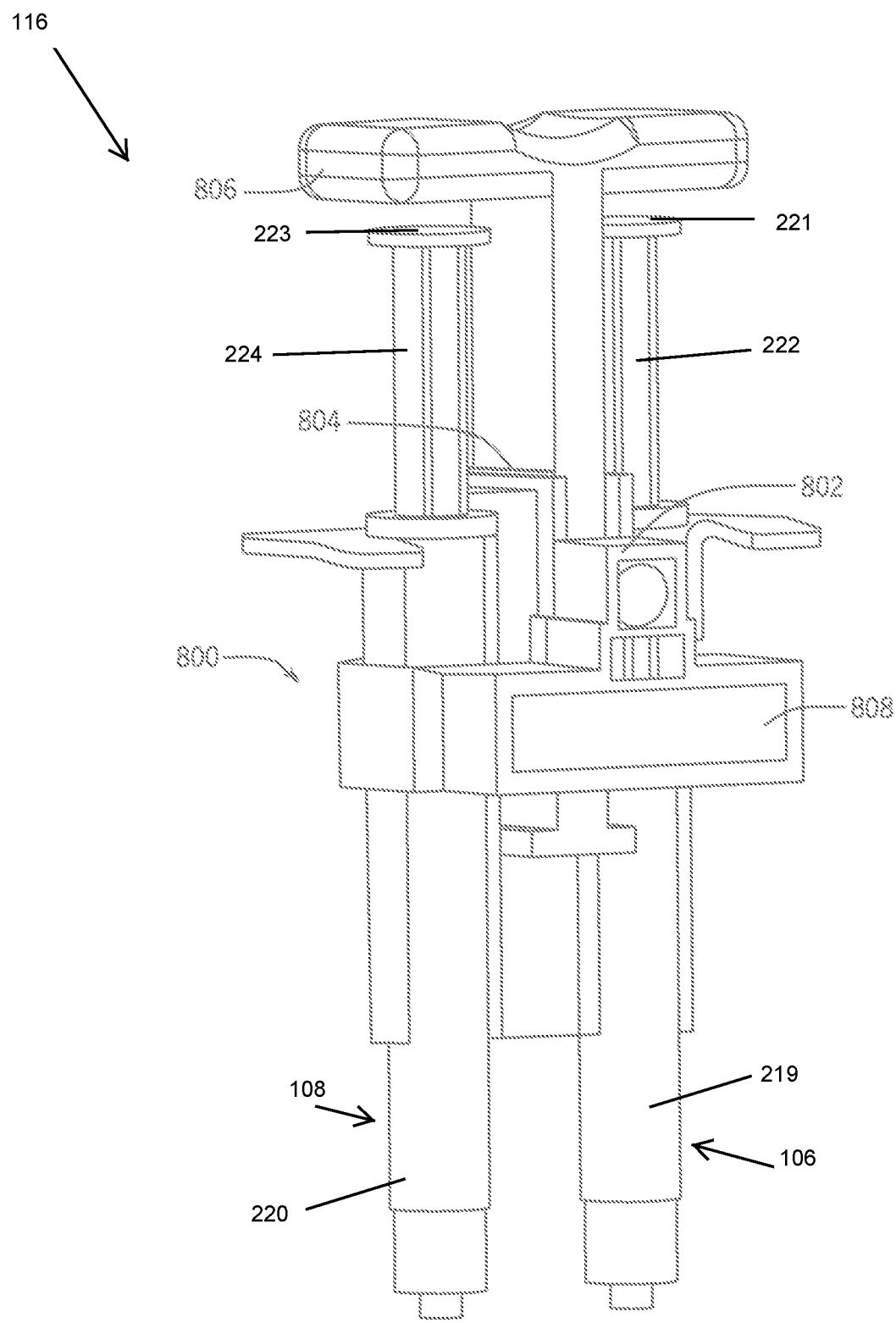
FIG. 6 is a drawing of an injection load monitoring device on a multi-barrel delivery syringe in an aspect.
Figure 7A:
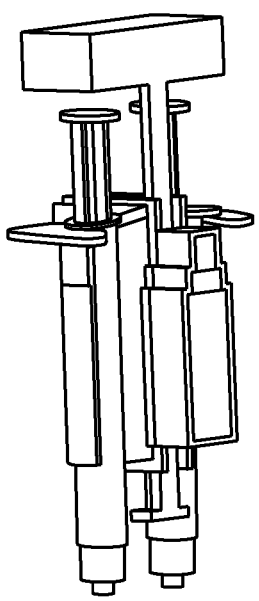
FIGS. 7A-F are drawings of the injection load monitoring device with a multi-barrel delivery syringe in various aspects.
Figure 7B:
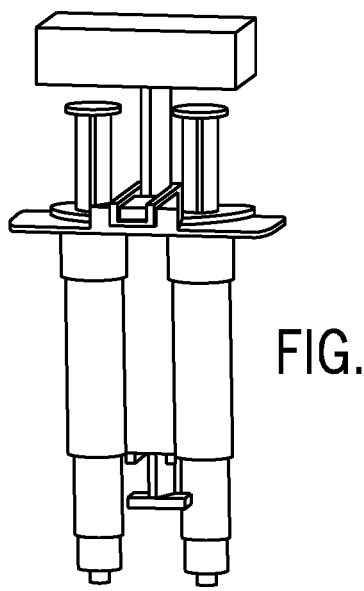
Figure 7C:
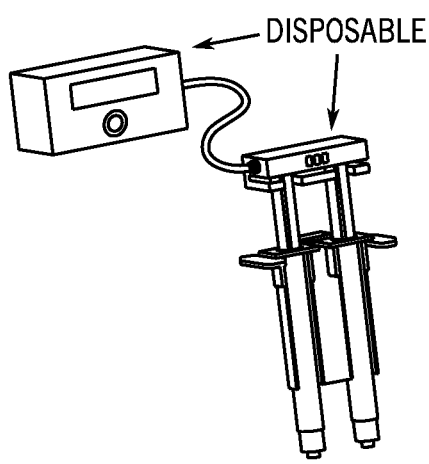
Figure 7D:
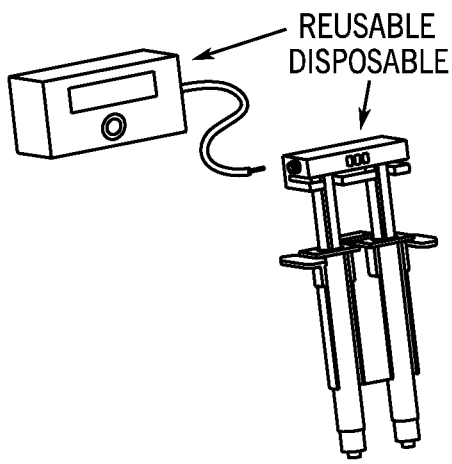
Figure 7E:
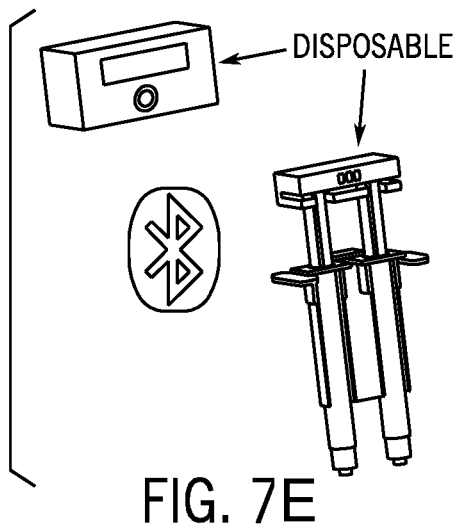
Figure 7F:
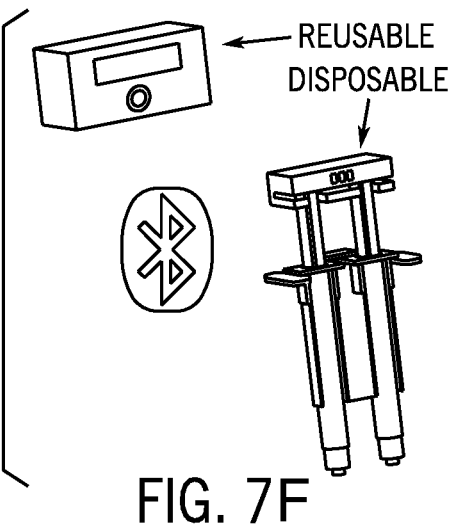

In another aspect, the injection preparation device 100 may further include an injection load monitoring device 800 (shown in FIGS. 6 and 7A-7F) to reversibly couple to a delivery syringe 116. The injection load monitoring device 800 may include a mechanical load sensor 802 having an amplifier and an electrical coupling coupled thereto for coupling to a pressure display unit; a syringe adapter 804 coupled to the mechanical load sensor, the syringe adapter having a first surface configured to engage an outward end portion of a plunger rod of a plunger rod assembly of the delivery syringe; and a finger plate 806 coupled to the mechanical load sensor. The mechanical load sensor 802 may be selected from a miniature or subminiature load cell and a piezoresistive mechanical load sensor. In an aspect, the mechanical load sensor 802 may be operable for measuring a compression load of up to about 100 lb. The mechanical load display unit 808 may display a visual alarm, an auditory alarm, or both in response to the mechanical load applied to the delivery syringe. In an aspect, the mechanical load display unit 808 may be directly coupled to the syringe adapter or finger plate as shown in FIG. 6. Alternatively, as depicted in FIGS. 7A to 7B, the pressure display unit 808 may be configured for wired or wireless communication with the mechanical load sensor 802.

Figure 3:
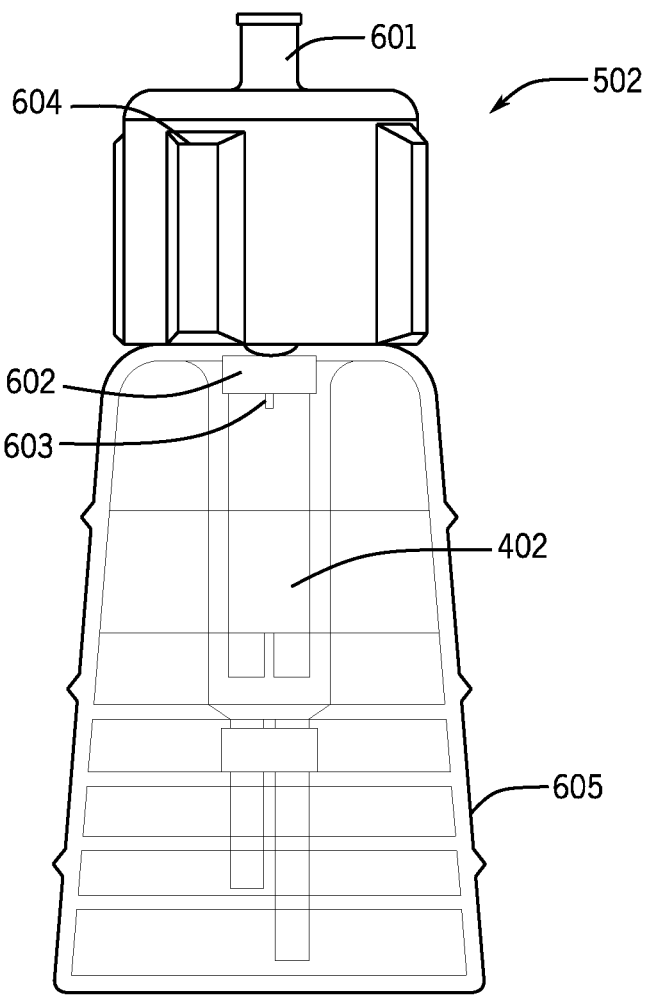
FIG. 3 is a front view of one aspect of the cell transfer container with a cell storage container.
Figure 4:
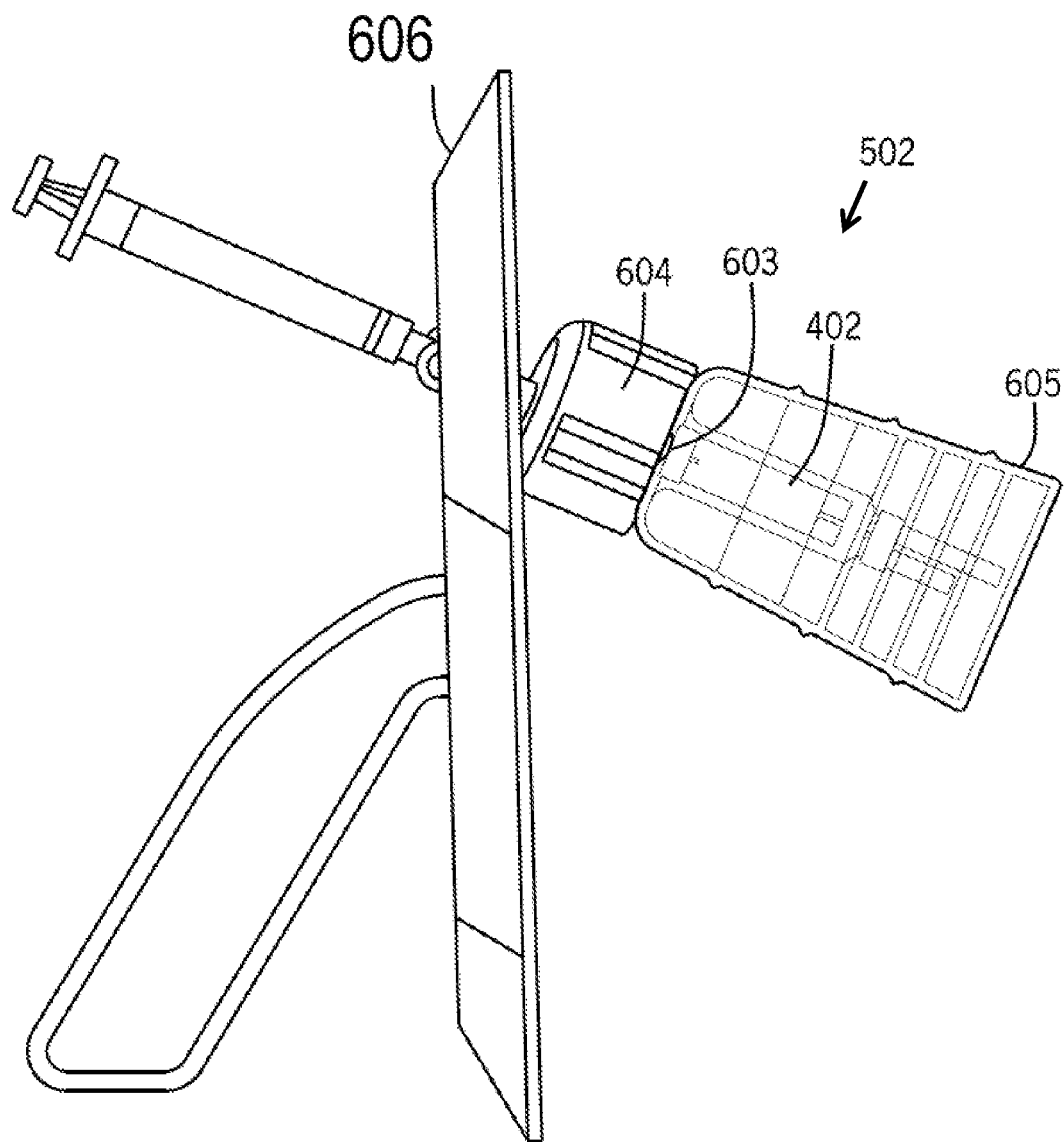
FIG. 4 is a drawing of a second cell transfer container with a cell storage container in one aspect.
Figure 5:
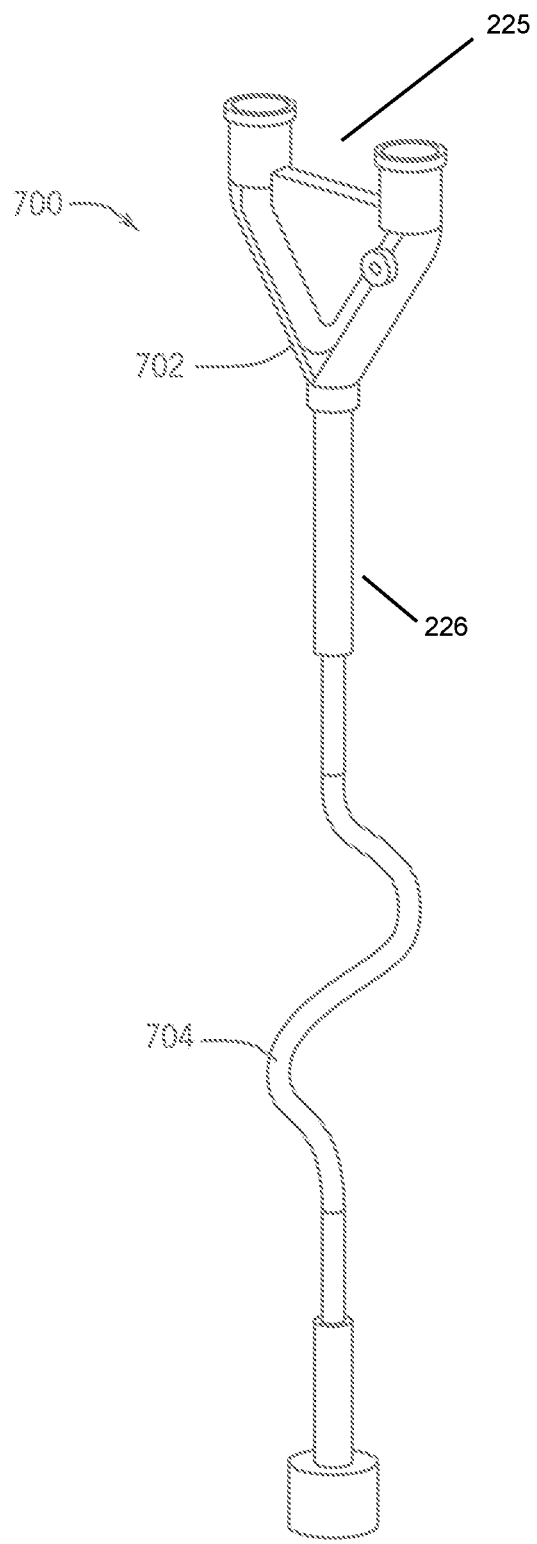
FIG. 5 is a drawing of a Y-connector for coupling to the delivery syringe and dual lumen cannula.

FIGS. 3 and 4 are drawings of various aspects of a cell transfer container 502 that may be used when transferring the cells from a cell storage container 402 to the cell transfer syringe 204. In an aspect, the present disclosure provides a cell transfer container 502 for use with a cell storage container 402 having an opening covered by a sterile seal 602 capable of penetration by a hollow needle. In one aspect, the cell storage container may be a cryovial. For example, the cell storage container may be used to store frozen cells. The cells may remain sterile through the sterile seal on the cell storage container. The cell storage container may be sterile inside the container and not sterile on the outside of the container. In an aspect, the cell transfer container may include the cell storage container, as shown in FIG. 3.

The cell transfer container 502 may include a body 604 having a first surface and a second surface and define an opening therethrough from the first surface to the second surface. In an aspect, the opening may have a rim. The cell transfer container 502 may further include a substantially tubular projection 605 from the first surface defining a wall surrounding the opening. In an aspect, the hollow needle 603 may be disposed perpendicular to the first surface from within the substantially tubular projection, wherein the hollow needle is fluidly connected to a connector port 601. The hollow needle 603 may be coupled to the rim of the opening and may have a length less than or equal to a depth of the tubular projection 605 from the first surface. The cell transfer container 502 may include a connector port 601 projecting from the body second surface. The connector port may define a wall surrounding the opening and the connector port may engage a syringe barrel. The connector port 601 may include a female luer port to reversibly engage a male luer-tipped syringe. The cell storage container 402 may connect to the body 604 via the hollow needle 603. For example, the needle 603 may puncture the seal 602 of the cell storage container 402 such that the contents of the cell storage container may be removed through the connector port 601 via the needle 603.

In an aspect, the body 604 may further comprise a substantially planar member 606 as shown in FIG. 4 for further assisting with the sterile transfer of cells from the cell storage container to the cell transfer syringe. The wall of the substantially tubular projection may define an opening therethrough so that the contents of the cell storage container 402 may be visible when the cell transfer container 502 is in use to penetrate the seal by contacting the seal with the hollow needle. The cell transfer container 502 may include a removable adhesive sterile barrier disposed over the opening through the body.

In another aspect, any combination described herein may include a cell storage container 402 and further include a prepared cell composition. The prepared cell composition may be stored within the cell storage container. The prepared cell composition may include but is not limited to cells selected from neuronal stem cells, chondrocytes, notochordal cells, chondrogenic cells, mesenchymal stem cells, hematopoietic stem cells, and any pluripotent stem cells including embryonic and induced pluripotent stem cells. The prepared cell composition may include but is not limited to mesenchymal stem cells derived from at least one of bone marrow, adipose tissue, synovium, periosteum, post-partum connective tissue, placenta, cord blood, and umbilical cord. In a non-limiting example, a prepared cell composition can comprise culture-expanded juvenile cartilage cells which are then combined for injection with a protein-based carrier such as fibrin.

A fibrin carrier may be prepared for example by combining thrombin and fibrinogen which react to form fibrin. It will be understood that once combined, thrombin and fibrinogen react quickly to form fibrin. Thus for example the devices, systems and methods described herein can be used to conveniently combine a prepared cell composition with a fibrin carrier which is itself prepared by a combination (of thrombin and fibrinogen). In a non-limiting example, the devices, systems and methods described herein may be used to conveniently prepare and then inject NuQu® into an intervertebral disc. NuQu® is a cell-based composition of culture-expanded juvenile cartilage chondrocytes in a fibrin carrier, as described for example in U.S. Pat. No. 7,879,604, the entire disclosure of which is herein incorporated by reference.

Thus, for example, the carrier syringe 104 may include two barrels and a double-barrel plunger rod assembly 118 configured to transfer a first predetermined amount of a first carrier component and a second predetermined amount of a second carrier component. The double-barrel plunger rod assembly 118 may include a first plunger rod for slidably engaging the first barrel of the carrier syringe 104 and a second plunger rod for slidably engaging the second barrel of the carrier syringe 104, where the first plunger rod is shorter than the second plunger rod so that the first predetermined amount of the first carrier component is less than the second predetermined amount of the second carrier component.

In an aspect, the first carrier component may be thrombin and the second carrier component may be fibrinogen, which when combined form fibrin. Other such two-component carriers can be used. Non-limiting examples of a first carrier component include thrombin, fibrinogen, poly(ethylene glycol) (PEG), poly(ethylene oxide) (PEO), poly(vinyl alcohol) (PVA), PEG-polystyrene copolymers (PEG)-(PST), polylactic acid (PLA), ethylene glycol-lactic acid copolymers, ethylene glycol-lactic acid-caprolactone copolymers, poly (d,l-lactide-co-ε-caprolactone), (poly)-anhydrides, anhydrides, urethanes, polysaccharides, dextran, collagen, hyaluronic acid, diethyl fumarate/poly(propylene fumarate), chitosan, a caprolactone polymer such as polycaprolactone (PCL), polyglycolic acid (PGA), or a copolymer of polylactic acid and polyglycolic acid (PLGA), and any combination thereof. In another aspect, the first carrier component may be a photoactive polymerizing polymer. Non-limiting examples of photoactive polymerizing polymers or monomers include collagen such as high density collagen, styrene, N-vinylpyrrolidone, acrylates, epoxides, urethanes, polyethers, and polyesters. In an aspect, the first carrier component may further include a photoinitiator. In another aspect, the second carrier component may include a photoinitiator. Non-limiting examples of photoinitiators include Diazopyruvate, Rose Bengal, riboflavin, riboflavin 5-monophosphate sodium salt dehydrate, m-tetrahydroxyphenylchlorin (mTHPC), benzophenone, xanthones, quinones, benzoin ethers, acetophenones, benzoyl oximes, and acylphosphines.

In any of the devices, kits and methods described herein, a non-limiting example use of a photoactive polymerizing polymer is as follows: a first carrier component and a second component can be prepared in any way which, when the two carrier components are combined, combines a photoactive polymerizing polymer and a photinitiator. In another aspect, only a first carrier component may be used. Alternatively, the first carrier component can include both a photoactive polymerizing polymer and a photoinitiator, and the second carrier component can include other materials as detailed elsewhere herein. For example the photoactive polymerizing polymer can be high density collagen (HDC) and the photoinitiator can be riboflavin. Once combined, the photoactive polymerizing polymer and photinitiator are then exposed to an appropriate wavelength of light given the selected photoinitiator. For example, if HDC and riboflavin are used, once combined the HDC is photochemically cross-linked by exposure to an appropriate wavelength of light for riboflavin, about 458 nm. The resulting photochemical cross-linking of the HDC provides a gel scaffold that promotes cell viability and reduces gel contraction.

In various aspects, the first predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. The second predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. In one aspect, the first predetermined amount may be about 0.6 cc and the second predetermined amount may be about 1.1 cc.

In any of the devices, kits and methods described herein, the first carrier component, second carrier component, or cell composition may optionally include one or more growth factors, osteostimulative agents, and/or bone morphogenetic proteins, which may be obtained by prior isolation from allogenic bone. Non-limiting examples of such growth factors that may be included into a first or second carrier component or cell composition of the present teachings include a member of the TGF-β superfamily, such as TGF-β1, TGF-β2, TGF-β3, or a bone morphogenetic protein (BMP); a growth differentiation factor; ADMP-1; a fibroblast growth factor (FGF) such as acidic FGF or basic FGF; a member of the hedgehog family of proteins, such as indian hedgehog, sonic hedgehog, or desert hedgehog; a platelet-derived growth factor, an interleukin; a colony-stimulating factor; an activin; a member of the insulin-like growth factor (IGF) family, such as IGF-I or IGF-II; a member of the platelet-derived growth factor (PDGF) family, such as PDGF-AP, PDGF-BB and PDGF-AA; a member of the interleukin (IL) family, such as IL-1, IL-2, IL-3, IL-4, IL-5 or IL-6; or a member of the colony-stimulating factor (CSF) family, such as CSF-1, G-CSF, and GM-CSF. A growth factor may be a growth factor obtained from a tissue source, or can be a recombinant growth factor produced in vitro, in a cell culture, or in a microorganism using standard molecular biology techniques. In some aspects, a growth factor may be a bone morphogenetic protein, such as, in non-limiting example, BMP-1, BMP-2, BMP-3, BMP-4, BMP-5, BMP-6 or BMP-7. Any such growth factors may for example be obtained by prior isolation from bone tissue including allogenic bone tissue. For example, one or more growth factors such as one or more BMPs may be isolated from allogenic bone and incorporated in the first carrier component, second carrier component, or cell composition.

The first carrier component, second carrier component, or cell composition as described herein may comprise, in addition to or instead of a growth factor, nutritional factors, hormones, peptides/proteins, or polysaccharides. Nutritional factors may include, but are not limited to, fatty acids, calcium, dextrose, glucose, glutamine, and vitamins such as vitamin A, B complex vitamins, vitamin C, vitamin D, vitamin E, or vitamin K. Hormones may include, but are not limited to, estrogen, testosterone, growth hormone, and thyroid hormone. Non-limiting examples of peptides or proteins include amino acids, link protein, GHK-copper peptide, BMP-13, BMP-14, PLAB, bone marrow aspirate lysate, and platelet lysate. Non-limiting examples of polysaccharides or monosaccharides includes carbohydrates, such as glucose or polymers thereof, dextran, hyaluronic acid (HyA), oligosaccharides of HyA, heparin, heparan sulfate, N-acetyl-glucosamine, and marine sulfated polysaccharides.

ii. 5-Inlet Injection Preparation Device

Figure 2:
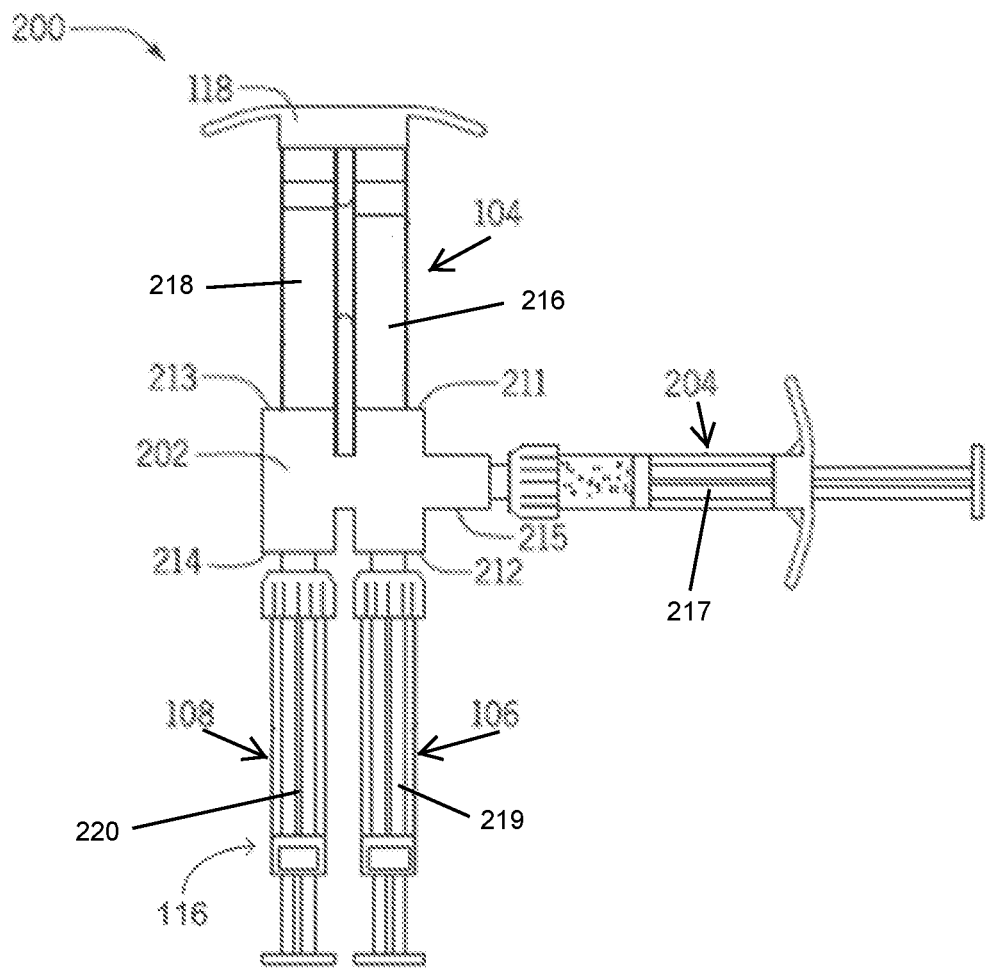
FIG. 2 is a top view of a five-inlet injection preparation device with a multi-barrel carrier syringe and a multi-barrel delivery syringe.

FIG. 2 is a drawing of an injection preparation device with five inlets 200. In one aspect, the five-inlet injection preparation device 200 includes a body 202 to reversibly engage a multi-barrel carrier syringe 104, a cell transfer syringe 204, a cell delivery syringe 106 and a carrier delivery syringe 108, the body 202 including a first transfer portion defining a first inlet 211 to reversibly couple to a first barrel 216 of the multi-barrel carrier syringe 104, a second inlet 212 to reversibly couple to a barrel 218 of the cell delivery syringe 106, and a fifth inlet 215 to reversibly couple to a barrel 217 of the cell transfer syringe 204, and a second transfer portion defining a third inlet 213 to reversibly couple to a second barrel 218 of the multi-barrel carrier syringe 104, a fourth inlet 214 to reversibly couple to a barrel 220 of the carrier delivery syringe 108. The first, second, and fifth inlets 211, 212, 215 communicate through a first conduit (not shown) through the body 202 and the third 213 and fourth inlets 214 communicate through a second conduit (not shown) through the body 202. At least one of the first, second, third, fourth and fifth inlets 211-215 may include a female connector port projecting from the body 202, where each female connector port may receive the injection end of the first barrel 216 of the carrier syringe 104, the second barrel 216 of the carrier syringe 104, the injection end of a barrel 219 of the cell delivery syringe 106, or the injection end of the barrel 220 of the carrier delivery syringe 108. At least one of the first, second, third, fourth and fifth inlets 211-215 may include a male connector port projecting from the body 202, where each male connector port may reversibly engage a female connector coupled to the first barrel 216 of the carrier syringe 104, the second barrel 216 of the carrier syringe 104, the injection end of the barrel 219 of the cell delivery syringe 106, or the injection end of the barrel 220 of the carrier delivery syringe 108. In an aspect, at least one of the first, second, third, fourth and fifth inlets 211-215 may include a luer connector. In an aspect, the first transfer portion may include a two-way valve (not shown) to limit a fluid path between the first and second inlets 211, 212 or between the second and fifth inlets 211, 215. In another aspect, the third inlet 213 defined by the second transfer portion may include a one-way (not shown) valve.

In another aspect, as illustrated in FIG. 2, the present disclosure provides a five-inlet injection preparation device 200, the cell delivery syringe 106 and the carrier delivery syringe 108 may be multiple barrels of a multi-barrel delivery syringe 116. This aspect may include a body 202 adapted to reversibly couple to a multi-barrel carrier syringe 104, a multi-barrel delivery syringe 116 comprising a cell delivery syringe 106 and a carrier delivery syringe 108, and a cell transfer syringe 204, the body 202 having a first transfer portion defining a first inlet 211 to reversibly couple to a first barrel 216 of the multi-barrel carrier syringe 104, a second inlet 212 to reversibly couple to a barrel 218 of the cell delivery syringe 106, and a fifth inlet 215 to reversibly couple to a barrel 217 of the cell transfer syringe 204, and a second transfer portion defining a third inlet 213 configured to reversibly couple to a second barrel 218 of the multi-barrel carrier syringe 104, a fourth inlet 214 configured to reversibly couple to a barrel 220 of the carrier delivery syringe 108. The first inlet 211, second inlet 212 and fifth inlet 215 communicate through a first conduit through the body 202 and the third 213 and fourth inlets 214 communicate through a second conduit through the body 202. At least one of the first, second, third, fourth and fifth inlets 211-215 may include a female connector port projecting from the body 202, where each female connector port may receive the injection end of the first barrel 216 of the carrier syringe 104, the second barrel 216 of the carrier syringe 104, the injection end of a barrel 219 of the cell delivery syringe 106, or the injection end of the barrel 220 of the carrier delivery syringe 108. At least one of the first, second, third, fourth and fifth inlets 211-215 may include a male connector port projecting from the body 202, each male connector port may reversibly engage a female connector coupled to the first barrel 216 of the carrier syringe 104, the second barrel 216 of the carrier syringe 104, the injection end of the barrel 219 of the cell delivery syringe 106, or the injection end of the barrel 220 of the carrier delivery syringe 108. In one aspect, at least one of the first, second, third, fourth and fifth inlets 211-215 may include a luer connector. The first transfer portion may include a two-way valve (not shown) to limit a fluid path between the first 211 and second inlets 212 or between the first 211 and fifth inlets 215. The second inlet 212 defined by the second transfer portion may include a one-way valve (not shown).

In another aspect, the injection preparation device 100 may further include an injection load monitoring device 800 (shown in FIGS. 6 and 7A-7F) to reversibly couple to a delivery syringe 116. The injection load monitoring device 800 may include a mechanical load sensor 802 having an amplifier (not shown) and an electrical coupling (not shown) coupled thereto for coupling to a pressure display unit (not shown); a syringe adapter 804 coupled to the mechanical load sensor 802, the syringe adapter having a first surface (not shown) configured to engage an outward end portion 221 of a first plunger rod of a plunger rod assembly of the delivery syringe 222 slidably engaging the barrel 219 of the cell delivery syringe 106 and an outward end portion 223 of a second plunger rod 224 slidably engaging the barrel 220 of the carrier delivery syringe 108; and a finger plate 806 coupled to the mechanical load sensor. The mechanical load sensor 802 may be selected from a miniature or subminiature load cell and a piezoresistive mechanical load sensor. In an aspect, the mechanical load sensor 802 may be operable for measuring a compression load of up to about 100 lb. The mechanical load display unit 808 may display a visual alarm, an auditory alarm, or both in response to the mechanical load applied to the delivery syringe. In an aspect, the mechanical load display unit 808 may be directly coupled to the syringe adapter or finger plate as shown in FIG. 6. Alternatively, as depicted in FIGS. 7A to 7F, the pressure display unit 808 may be configured for wired or wireless communication with the mechanical load sensor 802.

FIGS. 3 and 4 are drawings of various aspects of a cell transfer container 502 that may be used when transferring the cells from a cell storage container 402 to the cell transfer syringe 204. In an aspect, the present disclosure provides a cell transfer container 502 for use with a cell storage container 402 having an opening covered by a sterile seal 602 capable of penetration by a hollow needle. In one aspect, the cell storage container may be a cryovial. For example, the cell storage container may be used to store frozen cells. The cells may remain sterile through the sterile seal on the cell storage container. The cell storage container may be sterile inside the container and not sterile on the outside of the container. In an aspect, the cell transfer container may include the cell storage container, as shown in FIG. 3.

The cell transfer container 502 may include a body 604 having a first surface and a second surface and define an opening therethrough from the first surface to the second surface. In an aspect, the opening may have a rim. The cell transfer container 502 may further include a substantially tubular projection 605 from the first surface defining a wall surrounding the opening. In an aspect, the hollow needle 603 may be disposed perpendicular to the first surface from within the substantially tubular projection, where the hollow needle is fluidly connected to a connector port 601. The hollow needle 603 may be coupled to the rim of the opening and may have a length less than or equal to a depth of the tubular projection 605 from the first surface. The cell transfer container 502 may include a connector port 601 projecting from the body second surface. The connector port may define a wall surrounding the opening and the connector port may engage a syringe barrel. The connector port 601 may include a female luer port to reversibly engage a male luer-tipped syringe. The cell storage container 402 may connect to the body 604 via the hollow needle 603. For example, the needle 603 may puncture the seal 602 of the cell storage container 402 such that the contents of the cell storage container may be removed through the connector port 601 via the needle 603.

In an aspect, the body 604 may further comprise a substantially planar member 606 as shown in FIG. 4 for further assisting with the sterile transfer of cells from the cell storage container to the cell transfer syringe. The wall of the substantially tubular projection may define an opening therethrough so that the contents of the cell storage container 402 may be visible when the cell transfer container 502 is in use to penetrate the seal by contacting the seal with the hollow needle. The cell transfer container 502 may include a removable adhesive sterile barrier disposed over the opening through the body.

In another aspect, any combination described herein may include a cell storage container 402 and further include a prepared cell composition. The prepared cell composition may be stored within the cell storage container. The prepared cell composition may include but is not limited to cells selected from neuronal stem cells, chondrocytes, notochordal cells, chondrogenic cells, mesenchymal stem cells, hematopoietic stem cells, and any pluripotent stem cells including embryonic and induced pluripotent stem cells. The prepared cell composition may include but is not limited to mesenchymal stem cells derived from at least one of bone marrow, adipose tissue, synovium, periosteum, post-partum connective tissue, placenta, cord blood, and umbilical cord. In a non-limiting example, a prepared cell composition can comprise culture-expanded juvenile cartilage cells which are then combined for injection with a protein-based carrier such as fibrin.

In an aspect, the carrier syringe 104 may include two barrels and a double-barrel plunger rod assembly 118 configured to transfer a first predetermined amount of a first carrier component and a second predetermined amount of a second carrier component. The double-barrel plunger rod assembly 118 may include a first plunger rod for slidably engaging the first barrel of the carrier syringe 104 and a second plunger rod for slidably engaging the second barrel of the carrier syringe 104, where the first plunger rod is shorter (not shown) than the second plunger rod so that the first predetermined amount of the first carrier component is less than the second predetermined amount of the second carrier component.

In an aspect, the first carrier component may be thrombin and the second carrier component may be fibrinogen. Non-limiting examples of the first carrier component include thrombin, fibrinogen, poly(ethylene glycol) (PEG), poly (ethylene oxide) (PEO), poly(vinyl alcohol) (PVA), PEG-polystyrene copolymers (PEG)-(PST), polylactic acid (PLA), ethylene glycol-lactic acid copolymers, ethylene glycol-lactic acid-caprolactone copolymers, poly(d,l-lactide-co-ε-caprolactone), (poly)-anhydrides, anhydrides, urethanes, polysaccharides, dextran, collagen, hyaluronic acid, diethyl fumarate/poly(propylene fumarate), chitosan, a caprolactone polymer such as polycaprolactone (PCL), polyglycolic acid (PGA), or a copolymer of polylactic acid and polyglycolic acid (PLGA), and any combination thereof. In another aspect, the first carrier component may be a photoactive polymerizing polymer. Non-limiting examples of photoactive polymerizing polymers or monomers include collagen such as high density collagen, styrene, N-Vinylpyrrolidone, acrylates, epoxides, urethanes, polyethers, and polyesters. In an aspect, the first carrier component may further include a photoinitiator. In another aspect, the second carrier component may include a photoinitiator. Non-limiting examples of photoinitiators include Diazopyruvate, Rose Bengal, riboflavin, riboflavin 5-monophosphate sodium salt dehydrate, m-tetrahydroxyphenylchlorin (mTHPC), benzophenone, xanthones, quinones, benzoin ethers, acetophenones, benzoyl oximes, and acylphosphines.

In any of the devices, kits and methods described herein, a non-limiting example use of a photoactive polymerizing polymer is as follows: a first carrier component and a second component can be prepared in any way which, when the two carrier components are combined, combines a photoactive polymerizing polymer and a photinitiator. In another aspect, only a first carrier component may be used. Alternatively, the first carrier component can include both a photoactive polymerizing polymer and a photinitiator, and the second carrier component can include other materials as detailed elsewhere herein. For example the photoactive polymerizing polymer can be high density collagen (HDC) and the photoinitiator can be riboflavin. Once combined, the photoactive polymerizing polymer and photoinitiator are then exposed to an appropriate wavelength of light given the selected photoinitiator. For example, if HDC and riboflavin are used, once combined the HDC is photochemically cross-linked by exposure to an appropriate wavelength of light for riboflavin, about 458 nm. The resulting photochemical cross-linking of the HDC provides a gel scaffold that promotes cell viability and reduces gel contraction.

In various aspects, the first predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. The second predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. In one aspect, the first predetermined amount may be about 0.6 cc and the second predetermined amount may be about 1.1 cc.

In any of the devices, kits and methods described herein, the first carrier component, second carrier component, or cell composition may optionally include one or more growth factors, osteostimulative agents, and/or bone morphogenetic proteins, which may be obtained by prior isolation from allogenic bone. Non-limiting examples of such growth factors that may be included into a first or second carrier component or cell composition of the present teachings include a member of the TGF-β superfamily, such as TGF-β1, TGF-β2, TGF-β3, or a bone morphogenetic protein (BMP); a growth differentiation factor; ADMP-1; a fibroblast growth factor (FGF) such as acidic FGF or basic FGF; a member of the hedgehog family of proteins, such as indian hedgehog, sonic hedgehog, or desert hedgehog; a platelet-derived growth factor, an interleukin; a colony-stimulating factor; an activin; a member of the insulin-like growth factor (IGF) family, such as IGF-I or IGF-II; a member of the platelet-derived growth factor (PDGF) family, such as PDGF-AP, PDGF-BB and PDGF-AA; a member of the interleukin (IL) family, such as IL-1, IL-2, IL-3, IL-4, IL-5 or IL-6; or a member of the colony-stimulating factor (CSF) family, such as CSF-1, G-CSF, and GM-CSF. A growth factor may be a growth factor obtained from a tissue source, or can be a recombinant growth factor produced in vitro, in a cell culture, or in a microorganism using standard molecular biology techniques. In some aspects, a growth factor may be a bone morphogenetic protein, such as, in non-limiting example, BMP-1, BMP-2, BMP-3, BMP-4, BMP-5, BMP-6 or BMP-7. Any such growth factors may for example be obtained by prior isolation from bone tissue including allogenic bone tissue. For example, one or more growth factors such as one or more BMPs may be isolated from allogenic bone and incorporated in the first carrier component, second carrier component, or cell composition.

The first carrier component, second carrier component, or cell composition as described herein may comprise, in addition to or instead of a growth factor, nutritional factors, hormones, peptides/proteins, or polysaccharides. Nutritional factors may include, but are not limited to, fatty acids, calcium, dextrose, glucose, glutamine, and vitamins such as vitamin A, B complex vitamins, vitamin C, vitamin D, vitamin E, or vitamin K. Hormones may include, but are not limited to, estrogen, testosterone, growth hormone, and thyroid hormone. Non-limiting examples of peptides or proteins include amino acids, link protein, GHK-copper peptide, BMP-13, BMP-14, PLAB, bone marrow aspirate lysate, and platelet lysate. Non-limiting examples of polysaccharides or monosaccharides includes carbohydrates, such as glucose or polymers thereof, dextran, hyaluronic acid (HyA), oligosaccharides of HyA, heparin, heparan sulfate, N-acetyl-glucosamine, and marine sulfated polysaccharides.

B. Injection Preparation Kits i. 4-Inlet Injection Preparation Kit

In various aspects, the present disclosure provides an injection preparation kit including the four-inlet injection preparation device 100 described herein above, and at least one of a multi-barrel carrier syringe 104, a cell transfer syringe 204, a multi-barrel delivery syringe 116, comprising a cell delivery syringe 106 and a carrier delivery syringe 108. At least one or more of the multi-barrel carrier syringe 104, cell transfer syringe 204, cell delivery syringe 106 and carrier delivery syringe 108 may be coupled to the body 102. In one aspect, the multi-barrel carrier syringe 104, cell delivery syringe 106 and carrier delivery syringe 108 may be coupled to the body 102. The carrier syringe 104 may include two barrels and a double-barrel plunger rod assembly 118 to transfer a first predetermined amount of a first carrier component and a second predetermined amount of a second carrier component. In an aspect, the kit may include the cell delivery syringe 106 and the carrier delivery syringe 108 or the cell transfer syringe 204. In one aspect, the cell transfer syringe 204 may be a single-barrel syringe.

In another aspect, the present disclosure provides an injection preparation kit including the four-inlet injection preparation device 100 described herein above, and at least one of the multi-barrel carrier syringe 104, the multi-barrel delivery syringe 116 and the cell transfer syringe 204. At least one or more of the multi-barrel carrier syringe 104, the multi-barrel delivery syringe 116 and the cell transfer syringe 204 may be coupled to the body 102. In one aspect, the multi-barrel carrier syringe 104 and the multi-barrel delivery syringe 116 may be coupled to the body 102. In another aspect, the multi-barrel delivery syringe 116 and the cell transfer syringe 204 may be coupled to the body. The multi-barrel delivery syringe 116 may include two barrels and a double-barrel plunger rod assembly. In an aspect, the injection preparation kit may include the multi-barrel delivery syringe 116 or the cell transfer syringe 204. In one aspect, the cell transfer syringe 204 may be a single-barrel syringe.

In another aspect, the present disclosure provides for an injection preparation kit for transferring a prepared cell composition from a cell storage container 402 to a cell transfer syringe 204. The cell transfer container 502 may be configured to fluidly connect the cell storage container 402 with the cell transfer syringe 204. The injection preparation kit may include at least the injection preparation device 100 described herein above and a cell transfer container 502. The cell transfer container 502 may include a body 604 having a first surface and a second surface and define an opening therethrough from the first surface to the second surface. In an aspect, the opening may have a rim. The cell transfer container 502 may further include a substantially tubular projection 605 from the first surface defining a wall surrounding the opening. In an aspect, the hollow needle 603 may be disposed perpendicular to the first surface from within the substantially tubular projection, where the hollow needle is fluidly connected to a connector port 601. The hollow needle 603 may be coupled to the rim of the opening and may have a length less than or equal to a depth of the tubular projection 605 from the first surface. The cell transfer container 502 may include a connector port 601 projecting from the body second surface. The connector port may define a wall surrounding the opening and the connector port may engage a syringe barrel. The connector port 601 may include a female luer port to reversibly engage a male luer-tipped syringe. The cell storage container 402 may connect to the body 604 via the hollow needle 603. For example, the needle 603 may puncture the seal 602 of the cell storage container 402 such that the contents of the cell storage container may be removed through the connector port 601 via the needle 603.

In an aspect, the body 604 may further comprise a substantially planar member 606 as shown in FIG. 4 for further assisting with the sterile transfer of cells from the cell storage container to the cell transfer syringe. The wall of the substantially tubular projection may define an opening therethrough so that the contents of the cell storage container 402 may be visible when the cell transfer container 502 is in use to penetrate the seal by contacting the seal with the hollow needle. The cell transfer container 502 may include a removable adhesive sterile barrier disposed over the opening through the body.

The injection preparation kit may include a cell storage container 402 including a substantially cylindrical body defining a central lumen, a first end and a second end. The first end may define a vent port and a fill port, and the second end may define an access port. The vent port, fill port and access port may communicate with the central lumen. In an aspect, a flexible sealing element may be over the access port. For example, a sterile seal 602 may be over the access port. The flexible sealing element may include a rubber septum. The cell storage container 402 may further include a cap configured to seal the fill opening, where the fill opening and access port communicate with the central lumen. The cell storage container 402 may have an inner surface and an outer surface, where the inner surface may be sterile and the outer surface may be non-sterile. The cell storage container 402 may contain a prepared cell composition for transfer to a cell transfer syringe. The second end may further define a connector port for reversibly engaging a connector port of a second device. In an aspect, the cell storage container 402 may operate with an automated filling machine for filling the central lumen of the cell storage container with the prepared cell composition. Then, the cell storage container may be connected to the cell transfer container.

In an aspect, the injection preparation kit may further include a Y-connector 700 to reversibly couple to a multi-barrel delivery syringe 116. The Y-connector may include a connector body 702 having a first end and a second end, the first end defining at least two connector inlets for reversibly coupling the Y-connector to the at least two barrels of the delivery syringe 116. The Y-connector may further include a dual lumen cannula 704 coupled to the second end of the connector body. In an aspect, a spinal needle may be coupled to the dual lumen cannula 704.

In an aspect, the injection preparation kit may further include a light source or light conduit, such as an optic fiber, to expose a photoactivated polymer(s) at or near the end of the dual lumen cannula 704. In one aspect, the light source and/or light conduit may run the length of the dual lumen cannula 704. In various aspects, the light source and/or light conduit may be integral or attached to the Y-connector 700, dual lumen cannula 704, spinal needle, or delivery syringe 116. During the repair of tissue it may be desired to use a light polymerizing polymer as a carrier component for the delivery of biologic cells or drugs. The advantage in this arrangement is a single carrier component with the mixed in biologic cells or drugs may be sufficient instead of needing a two part carrier that reacts together. In an aspect, the carrier component may be polymerized by light which may be delivered via an integrated fiber optic in or on the spinal needle. This may allow for a rapid hardening of the photo-active polymer so it does not migrate and provide structural support similar to the current properties of the disc annulus. It also may allow for the contouring of the repair by controlled delivery and hardening of the polymer. In another aspect, using a light source with a photoactive polymer may allow for the construction of geometric structures to fit the deflect shape.

In one aspect, the injection preparation kit may include a fiber optic endoscope through which the spinal needle may be passed. The endoscope may allow for illumination and viewing of the defects repair which may allow for the contouring (geometric construction) of the polymerized carrier component with mixed in biologic cells or drugs.

In another aspect, even if the carrier is multi-component and delivered via a multi-barrel delivery syringe 116, the polymerization rate of the delivered polymer may be 'tuned' via light intensity. In one aspect, the fiber optic may be integrated into the delivery syringe 116 with the polymer being exposed to the light at the syringe hub to spinal needle transition. In another aspect, the fiber optic may be integrated into the dual lumen cannula 704. In either aspect, this would initiate the reaction for polymer polymerization before the carrier component(s) enter the needle and thus would be reacting as it is progressing down the needle to be delivered. This may have the benefit of allowing for a lower profile (outer diameter) spinal needle for delivery.

In an aspect, the injection preparation kit may include an amount of the cell preparation. In another aspect, the present disclosure provides an injection preparation kit described herein further including an amount of at least a first carrier component. The kit may further include an amount of a second carrier component, where the amounts of the first and the second carrier components are packaged separately. The first and the second carrier components when combined may form a polymerized hydrogel.

In an aspect, the injection preparation kit may include the cell storage container 402 and further include a prepared cell composition. In an aspect, the prepared cell composition may be within the cell storage container. The prepared cell composition may include but is not limited to cells selected from neuronal stem cells, chondrocytes, notochordal cells, chondrogenic cells, mesenchymal stem cells, hematopoietic stem cells, and any pluripotent stem cells including embryonic and induced pluripotent stem cells. The prepared cell composition may include but is not limited to mesenchymal stem cells derived from at least one of bone marrow, adipose tissue, synovium, periosteum, post-partum connective tissue, placenta, cord blood, and umbilical cord.

In an aspect, the carrier syringe 104 may include two barrels and a double-barrel plunger rod assembly 118 configured to transfer a first predetermined amount of a first carrier component and a second predetermined amount of a second carrier component. The double-barrel plunger rod assembly 118 may include a first plunger rod for slidably engaging the first barrel of the carrier syringe and a second plunger rod for slidably engaging the second barrel of the carrier syringe, where the first plunger rod is shorter than the second plunger rod so that the first predetermined amount of the first carrier component is less than the second predetermined amount of the second carrier component.

In an aspect, the first carrier component may be thrombin and the second carrier component may be fibrinogen. Non-limiting examples of the first carrier component include thrombin, fibrinogen, poly(ethylene glycol) (PEG), poly(ethylene oxide) (PEO), poly(vinyl alcohol) (PVA), PEG-polystyrene copolymers (PEG)-(PST), polylactic acid (PLA), ethylene glycol-lactic acid copolymers, ethylene glycol-lactic acid-caprolactone copolymers, poly(d,l-lactide-co-ε-caprolactone), (poly)-anhydrides, anhydrides, urethanes, polysaccharides, dextran, collagen, hyaluronic acid, diethyl fumarate/poly(propylene fumarate), chitosan, a caprolactone polymer such as polycaprolactone (PCL), polyglycolic acid (PGA), or a copolymer of polylactic acid and polyglycolic acid (PLGA), and combinations thereof. In another aspect, the first carrier component may be a photoactive polymerizing polymer. Non-limiting examples of photoactive polymerizing polymers or monomers include collagen, styrene, N-Vinylpyrrolidone, acrylates, epoxides, urethanes, polyethers, and polyesters. In an aspect, the first carrier component may further include a photoinitiator. In another aspect, the second carrier component may include a photoinitiator. Non-limiting examples of photoinitiators include Diazopyruvate, Rose Bengal, riboflavin, riboflavin 5-monophosphate sodium salt dehydrate, m-tetrahydroxyphenylchlorin (mTHPC), benzophenone, xanthones, quinones, benzoin ethers, acetophenones, benzoyl oximes, and acylphosphines.

In various aspects, the first predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. The second predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. In one aspect, the first predetermined amount may be about 0.6 cc and the second predetermined amount may be about 1.1 cc.

In any of the devices, kits and methods described herein, the first carrier component, second carrier component, or cell composition may optionally include one or more growth factors, osteostimulative agents, and/or bone morphogenetic proteins, which may be obtained by prior isolation from allogenic bone. Non-limiting examples of such growth factors that may be included into a first or second carrier component or cell composition of the present teachings include a member of the TGF-β superfamily, such as TGF-β1, TGF-β2, TGF-β3, or a bone morphogenetic protein (BMP); a growth differentiation factor; ADMP-1; a fibroblast growth factor (FGF) such as acidic FGF or basic FGF; a member of the hedgehog family of proteins, such as indian hedgehog, sonic hedgehog, or desert hedgehog; a platelet-derived growth factor, an interleukin; a colony-stimulating factor; an activin; a member of the insulin-like growth factor (IGF) family, such as IGF-I or IGF-II; a member of the platelet-derived growth factor (PDGF) family, such as PDGF-AP, PDGF-BB and PDGF-AA; a member of the interleukin (IL) family, such as IL-1, IL-2, IL-3, IL-4, IL-5 or IL-6; or a member of the colony-stimulating factor (CSF) family, such as CSF-1, G-CSF, and GM-CSF. A growth factor may be a growth factor obtained from a tissue source, or can be a recombinant growth factor produced in vitro, in a cell culture, or in a microorganism using standard molecular biology techniques. In some aspects, a growth factor may be a bone morphogenetic protein, such as, in non-limiting example, BMP-1, BMP-2, BMP-3, BMP-4, BMP-5, BMP-6 or BMP-7. Any such growth factors may for example be obtained by prior isolation from bone tissue including allogenic bone tissue. For example, one or more growth factors such as one or more BMPs may be isolated from allogenic bone and incorporated in the first carrier component, second carrier component, or cell composition.

The first carrier component, second carrier component, or cell composition as described herein may comprise, in addition to or instead of a growth factor, nutritional factors, hormones, peptides/proteins, or polysaccharides. Nutritional factors may include, but are not limited to, fatty acids, calcium, dextrose, glucose, glutamine, and vitamins such as vitamin A, B complex vitamins, vitamin C, vitamin D, vitamin E, or vitamin K. Hormones may include, but are not limited to, estrogen, testosterone, growth hormone, and thyroid hormone. Non-limiting examples of peptides or proteins include amino acids, link protein, GHK-copper peptide, BMP-13, BMP-14, PLAB, bone marrow aspirate lysate, and platelet lysate. Non-limiting examples of polysaccharides or monosaccharides includes carbohydrates, such as glucose or polymers thereof, dextran, hyaluronic acid (HyA), oligosaccharides of HyA, heparin, heparan sulfate, N-acetyl-glucosamine, and marine sulfated polysaccharides.

ii. 5-Inlet Injection Preparation Kit

In various aspects, the present disclosure provides an injection preparation kit including the five-inlet injection preparation device 200 described herein above, and at least one of a multi-barrel carrier syringe 104, a cell transfer syringe 204, a cell delivery syringe 106 and a carrier delivery syringe 108. At least one or more of the multi-barrel carrier syringe 104, cell transfer syringe 204, cell delivery syringe 106 and carrier delivery syringe 108 may be coupled to the body 202. In one aspect, the multi-barrel carrier syringe 104, cell delivery syringe 106 and carrier delivery syringe 108 may be coupled to the body 202. The injection preparation kit may include the multi-barrel carrier syringe 104. The carrier syringe 104 may include two barrels and a double-barrel plunger rod assembly 118 to transfer a first predetermined amount of a first carrier component and a second predetermined amount of a second carrier component. In an aspect, the kit may include the cell delivery syringe 106 and the carrier delivery syringe 108 or the cell transfer syringe 204. In one aspect, the cell transfer syringe 204 may be a single-barrel syringe.

In another aspect, the present disclosure provides an injection preparation kit including the five-inlet injection preparation device 200 described herein above and at least one of the multi-barrel carrier syringe 104, the multi-barrel delivery syringe 116 and the cell transfer syringe 204. At least one or more of the multi-barrel carrier syringe 104, the multi-barrel delivery syringe 116 and the cell transfer syringe 204 may be coupled to the body 202. In one aspect, the multi-barrel carrier syringe 104 and the multi-barrel delivery syringe 116 may be coupled to the body 202. In another aspect, the multi-barrel delivery syringe 116 and the cell transfer syringe 204 may be coupled to the body. The injection preparation kit may include the multi-barrel delivery syringe 116, where the delivery syringe 116 includes two barrels and a double-barrel plunger rod assembly. In an aspect, the injection preparation kit may include the cell transfer syringe 204. In one aspect, the cell transfer syringe 204 may be a single-barrel syringe.

In another aspect, the present disclosure provides for an injection preparation kit for transferring a prepared cell composition from a cell storage container 402 to a cell transfer syringe 204. The injection preparation kit may include at least the injection preparation device 200 described herein above and a cell transfer container 502. The cell transfer container 502 may be configured to fluidly connect the cell storage container 402 with the cell transfer syringe 204. The cell transfer container 502 may include a body 604 having a first surface and a second surface and define an opening therethrough from the first surface to the second surface. In an aspect, the opening may have a rim. The cell transfer container 502 may further include a substantially tubular projection 605 from the first surface defining a wall surrounding the opening. In an aspect, the hollow needle 603 may be disposed perpendicular to the first surface from within the substantially tubular projection, where the hollow needle is fluidly connected to a connector port 601. The hollow needle 603 may be coupled to the rim of the opening and may have a length less than or equal to a depth of the tubular projection 605 from the first surface. The cell transfer container 502 may include a connector port 601 projecting from the body second surface. The connector port may define a wall surrounding the opening and the connector port may engage a syringe barrel. The connector port 601 may include a female luer port to reversibly engage a male luer-tipped syringe. The cell storage container 402 may connect to the body 604 via the hollow needle 603. For example, the needle 603 may puncture the seal 602 of the cell storage container 402 such that the contents of the cell storage container may be removed through the connector port 601 via the needle 603.

In an aspect, the body 604 may further comprise a substantially planar member 606 as shown in FIG. 4 for further assisting with the sterile transfer of cells from the cell storage container to the cell transfer syringe. The wall of the substantially tubular projection may define an opening therethrough so that the contents of the cell storage container 402 may be visible when the cell transfer container 502 is in use to penetrate the seal by contacting the seal with the hollow needle. The cell transfer container 502 may include a removable adhesive sterile barrier disposed over the opening through the body.

The injection preparation kit may include a cell storage container 402 including a substantially cylindrical body defining a central lumen, a first end and a second end. The first end may define a vent port and a fill port, and the second end may define an access port. The vent port, fill port and access port may communicate with the central lumen. In an aspect, a flexible sealing element may be over the access port. For example, a sterile seal 602 may be over the access port. The flexible sealing element may include a rubber septum. The cell storage container 402 may further include a cap configured to seal the fill opening, where the fill opening and access port communicate with the central lumen. The cell storage container 402 may have an inner surface and an outer surface, where the inner surface may be sterile and the outer surface may be non-sterile. The cell storage container 402 may contain a prepared cell composition for transfer to a cell transfer syringe. The second end may further define a connector port for reversibly engaging a connector port of a second device. In an aspect, the cell storage container 402 may operate with an automated filling machine for filling the central lumen of the cell storage container with the prepared cell composition. Then, the cell storage container may be connected to the cell transfer container.

In an aspect, the injection preparation kit may further include a Y-connector 700 to reversibly couple to a multi-barrel delivery syringe 116. The Y-connector may include a connector body 702 having a first end 225 and a second end 226, the first end 225 defining at least two connector inlets for reversibly coupling the Y-connector to the at least two barrels of the delivery syringe 116; a dual lumen cannula 704 coupled to the second end of the connector body; and a spinal needle (not shown) coupled to the dual lumen cannula 704.

In an aspect, the injection preparation kit may further include a light source or light conduit, such as an optic fiber, to expose a photoactivated polymer(s) at or near the end of the dual lumen cannula 704. In one aspect, the light source and/or light conduit may run the length of the dual lumen cannula 704. In various aspects, the light source and/or light conduit may be integral or attached to the Y-connector 700, dual lumen cannula 704, spinal needle (not shown), or delivery syringe 116. During the repair of tissue it may be desired to use a light polymerizing polymer as a carrier component for the delivery of biologic cells or drugs. The advantage in this arrangement is a single carrier component with the mixed in biologic cells or drugs may be sufficient instead of needing a two part carrier that reacts together. In an aspect, the carrier component may be polymerized by light which may be delivered via an integrated fiber optic in or on the spinal needle (not shown). This may allow for a rapid hardening of the photoactive polymer so it does not migrate and provide structural support similar to the current properties of the disc annulus. It also may allow for the contouring of the repair by controlled delivery and hardening of the polymer. In another aspect, using a light source with a photoactive polymer may allow for the construction of geometric structures to fit the deflect shape.

In one aspect, the injection preparation kit may include a fiber optic endoscope through which the spinal needle may be passed. The endoscope may allow for illumination and viewing of the defects repair which may allow for the contouring (geometric construction) of the polymerized carrier component with mixed in biologic cells or drugs.

In another aspect, even if the carrier is multi-component and delivered via a multi-barrel delivery syringe 116, the polymerization rate of the delivered polymer may be 'tuned' via light intensity. In one aspect, the fiber optic may be integrated into the delivery syringe 116 with the polymer being exposed to the light at the syringe hub to spinal needle transition. In another aspect, the fiber optic may be integrated into the dual lumen cannula 704. In either aspect, this would initiate the reaction for polymer polymerization before the carrier component(s) enter the needle and thus would be reacting as it is progressing down the needle to be delivered. This may have the benefit of allowing for a lower profile (outer diameter) spinal needle for delivery.

In an aspect, the injection preparation kit may further include an amount of the prepared cell composition. In another aspect, the present disclosure provides an injection preparation kit described herein further including an amount of at least a first carrier component. The kit may further including an amount of a second carrier component, where the amounts of the first and the second carrier components are packaged separately. The first and the second carrier components when combined form a polymerized hydrogel.

In an aspect, the injection preparation kit may include the cell storage container 402 and further include a prepared cell composition. In an aspect, the prepared cell composition may be within the cell storage container. The prepared cell composition may include but is not limited to cells selected from neuronal stem cells, chondrocytes, notochordal cells, chondrogenic cells, mesenchymal stem cells, hematopoietic stem cells, and any pluripotent stem cells including embryonic and induced pluripotent stem cells. The prepared cell composition may include but is not limited to mesenchymal stem cells derived from at least one of bone marrow, adipose tissue, synovium, periosteum, post-partum connective tissue, placenta, cord blood, and umbilical cord.

In an aspect, the carrier syringe 104 may include two barrels and a double-barrel plunger rod assembly 118 configured to transfer a first predetermined amount of a first carrier component and a second predetermined amount of a second carrier component. The double-barrel plunger rod assembly 118 may include a first plunger rod for slidably engaging the first barrel of the carrier syringe and a second plunger rod for slidably engaging the second barrel of the carrier syringe, where the first plunger rod is shorter than the second plunger rod so that the first predetermined amount of the first carrier component is less than the second predetermined amount of the second carrier component.

In an aspect, the first carrier component may be thrombin and the second carrier component may be fibrinogen. Non-limiting examples of the first carrier component include thrombin, fibrinogen, poly(ethylene glycol) (PEG), poly (ethylene oxide) (PEO), poly(vinyl alcohol) (PVA), PEG-polystyrene copolymers (PEG)-(PST), polylactic acid (PLA), ethylene glycol-lactic acid copolymers, ethylene glycol-lactic acid-caprolactone copolymers, poly(d,l-lactide-co-ε-caprolactone), (poly)-anhydrides, anhydrides, urethanes, polysaccharides, dextran, collagen, hyaluronic acid, diethyl fumarate/poly(propylene fumarate), chitosan, a caprolactone polymer such as polycaprolactone (PCL), polyglycolic acid (PGA), or a copolymer of polylactic acid and polyglycolic acid (PLGA), and combinations thereof. In another aspect, the first carrier component may be a photoactive polymerizing polymer. Non-limiting examples of photoactive polymerizing polymers or monomers include collagen, styrene, N-Vinylpyrrolidone, acrylates, epoxides, urethanes, polyethers, and polyesters. In an aspect, the first carrier component may further include a photoinitiator. In another aspect, the second carrier component may include a photoinitiator. Non-limiting examples of photoinitiators include Diazopyruvate, Rose Bengal, riboflavin, riboflavin 5-monophosphate sodium salt dehydrate, m-tetrahydroxyphenylchlorin (mTHPC), benzophenone, xanthones, quinones, benzoin ethers, acetophenones, benzoyl oximes, and acylphosphines.

In various aspects, the first predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. The second predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. In one aspect, the first predetermined amount may be about 0.6 cc and the second predetermined amount may be about 1.1 cc.

In any of the devices, kits and methods described herein, the first carrier component, second carrier component, or cell composition may optionally include one or more growth factors, osteostimulative agents, and/or bone morphogenetic proteins, which may be obtained by prior isolation from allogenic bone. Non-limiting examples of such growth factors that may be included into a first or second carrier component or cell composition of the present teachings include a member of the TGF-β superfamily, such as TGF-β1, TGF-β2, TGF-β3, or a bone morphogenetic protein (BMP); a growth differentiation factor; ADMP-1; a fibroblast growth factor (FGF) such as acidic FGF or basic FGF; a member of the hedgehog family of proteins, such as indian hedgehog, sonic hedgehog, or desert hedgehog; a platelet-derived growth factor, an interleukin; a colony-stimulating factor; an activin; a member of the insulin-like growth factor (IGF) family, such as IGF-I or IGF-II; a member of the platelet-derived growth factor (PDGF) family, such as PDGF-AP, PDGF-BB and PDGF-AA; a member of the interleukin (IL) family, such as IL-1, IL-2, IL-3, IL-4, IL-5 or IL-6; or a member of the colony-stimulating factor (CSF) family, such as CSF-1, G-CSF, and GM-CSF. A growth factor may be a growth factor obtained from a tissue source, or can be a recombinant growth factor produced in vitro, in a cell culture, or in a microorganism using standard molecular biology techniques. In some aspects, a growth factor may be a bone morphogenetic protein, such as, in non-limiting example, BMP-1, BMP-2, BMP-3, BMP-4, BMP-5, BMP-6 or BMP-7. Any such growth factors may for example be obtained by prior isolation from bone tissue including allogenic bone tissue. For example, one or more growth factors such as one or more BMPs may be isolated from allogenic bone and incorporated in the first carrier component, second carrier component, or cell composition.

The first carrier component, second carrier component, or cell composition as described herein may comprise, in addition to or instead of a growth factor, nutritional factors, hormones, peptides/proteins, or polysaccharides. Nutritional factors may include, but are not limited to, fatty acids, calcium, dextrose, glucose, glutamine, and vitamins such as vitamin A, B complex vitamins, vitamin C, vitamin D, vitamin E, or vitamin K. Hormones may include, but are not limited to, estrogen, testosterone, growth hormone, and thyroid hormone. Non-limiting examples of peptides or proteins include amino acids, link protein, GHK-copper peptide, BMP-13, BMP-14, PLAB, bone marrow aspirate lysate, and platelet lysate. Non-limiting examples of polysaccharides or monosaccharides includes carbohydrates, such as glucose or polymers thereof, dextran, hyaluronic acid (HyA), oligosaccharides of HyA, heparin, heparan sulfate, N-acetyl-glucosamine, and marine sulfated polysaccharides.

C. Injection Preparation Methods i. 4-Inlet Injection Preparation Methods

In an aspect, the present disclosure provides a method of preparing a multi-component injection, including obtaining a carrier syringe 104 including at least two barrels with a first carrier component in a first barrel and a second carrier component in a second barrel; coupling a first barrel of the carrier syringe 104 to the first inlet 111 of an injection preparation device 100, and a second barrel of the carrier syringe 104 to the third inlet 113 of the injection preparation device 100; coupling a cell delivery syringe 106 to the second inlet 112 of the injection preparation device 100; and coupling a carrier delivery syringe 108 to the fourth inlet 114 of the injection preparation device 100. The method may further include transferring the first carrier component from the first barrel of the carrier syringe 104 to the cell delivery syringe 106 through the first conduit of the injection preparation device 100 and transferring the second carrier component from the second barrel of the carrier syringe 104 to the carrier delivery syringe 108 through the second conduit of the injection preparation device 100. A dual plunger rod assembly 118 used with the carrier syringe 104 may be configured to transfer a predetermined amount of the first carrier component to the cell delivery syringe 106 and a predetermined amount of the second carrier component to the carrier delivery syringe 108. The method may further include coupling a cell transfer syringe 204 to the injection preparation device 100. In an aspect, the cell transfer syringe 204 may be coupled to the first inlet 111 of the injection preparation device 100. The method may further include removing the carrier syringe 104 from the injection preparation device 100 and coupling a cell transfer syringe 204 containing a cell composition to the injection preparation device 100. The first carrier component may be transferred from the cell delivery syringe 106 to the cell transfer syringe 204 though the first conduit, whereby the first carrier component is mixed with the cell composition to form a first cell/carrier mixture. The first cell/carrier mixture may then be transferred back to the cell delivery syringe 106 through the first conduit.

In another aspect, the present disclosure provides a method of preparing a multi-component injection, including filling a carrier syringe 104 including at least two barrels with a first carrier component in a first barrel and a second carrier component in a second barrel. The two barrels of the carrier syringe 104 may be coupled to the first 111 and third inlets 113 of an injection preparation device 100, and the two barrels of the multi-barrel delivery syringe 116 may be coupled to the second 112 and fourth inlets 114 of the injection preparation device 100. In an aspect, the method may include transferring the first carrier component from the first barrel of the carrier syringe 104 to a first barrel of the delivery syringe 116 through the first conduit of the injection preparation device, and transferring the second carrier component from the second barrel of the carrier syringe 104 to a second barrel of the delivery syringe 116 through the second conduit of the injection preparation device 100. A double-barrel plunger rod assembly 118 used with the carrier syringe 104 may be configured to transfer a predetermined amount of the first carrier component and a predetermined amount of the second carrier component to the delivery syringe 116. The method may further include removing the carrier syringe 104 from the injection preparation device 100 and coupling a cell transfer syringe 204 containing a cell composition to the injection preparation device 100. In an aspect, the method may include transferring the first carrier component from the first barrel of the delivery syringe 116 to the cell transfer syringe 204 though the first conduit, whereby the first carrier component is mixed with the cell composition to form a first cell/carrier mixture; and transferring the first cell/carrier mixture back to the first barrel of the delivery syringe 116 through the first conduit. The cell transfer syringe may be coupled to the first inlet of the of the injection preparation device. In an aspect, the method may further include decoupling the delivery syringe 116 from the injection preparation device 100, where the first barrel of the delivery syringe 116 contains the first cell/carrier mixture and the second barrel of the delivery syringe 116 contains the second carrier component.

The method may further include coupling the delivery syringe 116 to a Y-connector 700 having a stem portion, and ejecting the first cell/carrier mixture from the first barrel of the delivery syringe 116 or the cell delivery syringe 106 and the second carrier component from the second barrel of the delivery syringe 116 or the carrier delivery syringe 108 through the Y-connector 700, whereby the first cell/carrier mixture and the second carrier component are combined in the Y-connector stem portion to form a cell/carrier composition. The Y-connector 700 may be configured to reversibly couple to the cell delivery syringe 106 and to the carrier delivery syringe 108 or the multi-barrel delivery syringe 116. The Y-connector 700 includes a connector body 702 having a first end and a second end, the first end defining at least two connector inlets for reversibly coupling the Y-connector 700 to the cell delivery syringe 106 and the carrier delivery syringe 108 or to the at least two barrels of the delivery syringe 116. The method may further include coupling a dual lumen cannula 704 to the second end of the Y-connector body 702 and coupling a spinal needle to the dual lumen cannula 704.

In an aspect, the method may further include introducing a light source or light conduit, such as an optic fiber or endoscope, to expose photoactivated polymer(s) at or near the end of the dual lumen cannula. In one aspect, the light source and/or light conduit may run the length of the dual cannula. In various aspects, the light source and/or light conduit may be integral or attached to the Y-connector, dual cannula, spinal needle, or delivery syringe. During the repair of the spinal disc annulus it may be desired to use a light polymerizing polymer as a carrier for the delivery of biologic cells or drugs. The advantage in this arrangement is a single carrier component with the mixed in biologic cells or drugs may be sufficient instead of needing a two part carrier that reacts together. In an aspect, the carrier component may be polymerized by light which may be delivered via an integrated fiber optic in or on the spinal needle. This may allow for a rapid hardening of the photoactive polymer so it does not migrate and provide structural support similar to the current properties of the disc annulus. It also may allow for the contouring of the repair by controlled delivery and hardening of the polymer. In another aspect, using a light source with a photoactive polymer may allow for the construction of geometric structures to fit the deflect shape.

In one aspect, the method may include passing the spinal needle through a fiber optic endoscope. The endoscope may allow for illumination and viewing of the defects repair which may allow for the contouring (geometric construction) of the polymerized carrier component with mixed in biologic cells or drugs.

In another aspect, even if the carrier is multi-component and delivered via a multi-barrel delivery syringe, the polymerization rate of the delivered polymer may be 'tuned' via light intensity. In an aspect, the carrier component(s) may be exposed to light to initiate the reaction for polymer polymerization before the carrier component(s) enter the needle and thus would be reacting as it is progressing down the needle to be delivered. This may have the benefit of allowing for a lower profile (outer diameter) spinal needle for delivery.

The methods may further include injecting the cell/carrier composition into a tissue defect. In various aspects, the tissue may be, without limitation, bone, cartilage, tendon tissue, ligament tissue, soft tissue such as vascular tissue, dermal tissue or muscle tissue, neural tissue, or a combination thereof. In some other aspects, a site in need of tissue growth may include tendon tissue, ligament tissue, vascular tissue, dermal tissue, periodontal tissue, intervertebral disc tissue, hyaline cartilage, fibrous cartilage, elastic cartilage, a nerve tunnel or a combination thereof. In another aspect, the tissue may include but is not limited to bone, cartilage or soft tissue. In an aspect, the methods may further include injecting the cell/carrier composition into a degenerated intervertebral disc.

In various configurations, a site in need of tissue growth may include, without limitation, dermis, a rotator cuff tendon, an Achilles tendon, a ligament such as an anterior cruciate ligament (ACL), a posterior cruciate ligament, (PCL), a medial collateral ligament, a lateral collateral ligament or a periodontal figment, a sphincter such as an anal sphincter, a urethral sphincter, an esophageal sphincter or an antral sphincter, herniated tissue such as an abdominal hernia, a Cooper's hernia, a diaphragmatic hernia, an epigastric hernia, a femoral hernia, an incisional hernia, an inguinal hernia, an intervertebral disc hernia, a Littre's hernia, an obturator hernia, a pantaloon hernia, a perineal hernia, a properitoneal hernia, a Richter's hernia, a sciatic hernia, a sliding hernia, a Spigelian hernia or an umbilical hernia, an intervertebral disc nucleus, an intervertebral disc annulus, periosteal tissue, neural tissue such as central nervous system tissue (including spinal cord tissue) and demyelinated neural tissue, peripheral nervous system tissue, a nerve tunnel such as a nerve tunnel traversing bone tissue, a mitral valve, a tricuspid valve, an aortic heart valve, a pulmonary heart valve, vascular tissue comprising a stent, stenotic cardiovascular tissue, cartilage, costal cartilage, meniscus cartilage, epiglottic cartilage, laryngeal cartilage such as arytenoid cartilage, cricoid cartilage, cuneiform cartilage and corniculate cartilage, external ear cartilage, auditory tube cartilage, labral cartilage, articular cartilage, bone, bone defects/voids, muscle, and other soft tissues.

In an aspect, the method may further include monitoring the injection load using an injection load monitoring device 800 reversibly coupled to the cell delivery syringe 106 and the carrier delivery syringe 108 or the multi-barrel delivery syringe 116. In an aspect, the injection load monitoring device 800 may include a mechanical load sensor 802 having an amplifier and an electrical coupling coupled thereto for coupling to a pressure display unit 808; a syringe adapter 804 coupled to the mechanical load sensor 802 and a finger plate 806 coupled to the mechanical load sensor 802. The syringe adapter 804 may have a first surface configured to engage an outward end portion of a plunger rod of a plunger rod assembly of the delivery syringe 116 or the cell delivery syringe 106 and the carrier delivery syringe 108. In an aspect, the mechanical load sensor 802 may be selected from a miniature or subminiature load cell and a piezoresistive force sensor. The mechanical load sensor 802 may be operable for measuring a compression load of up to about 100 lb. In an aspect, the pressure display unit 808 may display a visual alarm, an auditory alarm, or both in response to the pressure applied to the delivery syringe 116. The pressure display unit 800 may be directly coupled to the syringe adapter 804 or finger plate 806. In an aspect, the pressure display unit 808 may be coupled to the mechanical load sensor wirelessly.

In another aspect, the method may include connecting a cell transfer container 502 to a cell storage container 402 by penetrating a needle through the opening covered by a sterile seal of the cell storage container 402. The cell transfer container 502 may engage a syringe barrel, such as the cell transfer syringe. In a non-limiting example, the connector port may use a female luer port to reversibly engage a male luer-tipped syringe. The wall of the substantially tubular projection may define an opening therethrough so that the contents of the cell storage container 402 may be visible when the cell transfer container 502 is in use to penetrate the seal by contacting the seal with the hollow needle.

In an aspect, the prepared cell composition may include but is not limited to cells selected from neuronal stem cells, chondrocytes, notochordal cells, chondrogenic cells, mesenchymal stem cells, hematopoietic stem cells, and any pluripotent stem cells, including embryonic and induced pluripotent stem cells. The prepared cell composition may include but is not limited to mesenchymal stem cells derived from at least one of bone marrow, adipose tissue, synovium, periosteum, post-partum connective tissue, placenta, cord blood, and umbilical cord. It should be understood that the methods encompass any method in which the cells selected for the cell/carrier composition match the tissue or tissues being repaired. Appropriate combinations of cells are also contemplated. For example, chondrogenic cells can be selected to repair cartilage tissue; osteogenic cells can be selected to repair bone; a combination of chondrogenic cells and osteogenic cells can be selected to repair damage to a combination of cartilage and bone; neural or neurogenic cells can be selected to repair cartilage nervous tissue.

In an aspect, the carrier syringe 104 may include two barrels and a double-barrel plunger rod assembly 118 configured to transfer a first predetermined amount of a first carrier component and a second predetermined amount of a second carrier component. The double-barrel plunger rod assembly 118 may include a first plunger rod for slidably engaging the first barrel of the carrier syringe and a second plunger rod for slidably engaging the second barrel of the carrier syringe, where the first plunger rod is shorter than the second plunger rod so that the first predetermined amount of the first carrier component is less than the second predetermined amount of the second carrier component.

In an aspect, the first carrier component may be thrombin and the second carrier component may be fibrinogen. Non-limiting examples of the first carrier component include thrombin, fibrinogen, poly(ethylene glycol) (PEG), poly (ethylene oxide) (PEO), poly(vinyl alcohol) (PVA), PEG-polystyrene copolymers (PEG)-(PST), polylactic acid (PLA), ethylene glycol-lactic acid copolymers, ethylene glycol-lactic acid-caprolactone copolymers, poly(d,l-lactide-co-ε-caprolactone), (poly)-anhydrides, anhydrides, urethanes, polysaccharides, dextran, collagen, hyaluronic acid, diethyl fumarate/poly(propylene fumarate), chitosan, a caprolactone polymer such as polycaprolactone (PCL), polyglycolic acid (PGA), or a copolymer of polylactic acid and polyglycolic acid (PLGA), and combinations thereof. In another aspect, the first carrier component may be a photoactive polymerizing polymer. Non-limiting examples of photoactive polymerizing polymers or monomers include collagen, styrene, N-Vinylpyrrolidone, acrylates, epoxides, urethanes, polyethers, and polyesters. In an aspect, the first carrier component may further include a photoinitiator. In another aspect, the second carrier component may include a photoinitiator. Non-limiting examples of photoinitiators include Diazopyruvate, Rose Bengal, riboflavin, riboflavin 5-monophosphate sodium salt dehydrate, m-tetrahydroxyphenylchlorin (mTHPC), benzophenone, xanthones, quinones, benzoin ethers, acetophenones, benzoyl oximes, and acylphosphines.

It should be understood therefore that the carrier, such as a protein carrier, used to deliver cells to target tissues in need of repair may be selected from a variety of natural and/or engineered proteins, the most commonly encountered being collagen. Additionally, in the presence of a suitable non-toxic photoactive agent, a light source can be applied to crosslink the carrier material containing a cell suspension, thereby fixing the cells within the construct and further anchoring the delivered structural matrix to exposed collagen fibrils within adjacent native tissue. Note that either continuous or pulsed delivery of the irradiation source may be utilized to enhance crosslinking as well as depth of desired cross-linking. Common such photoinitiators include but are not limited to: Diazopyruvate—330-400 nm light source; 0.1-0.5 mM riboflavin—475-480 nm xenon light source; 10-40 s; and m-tetrahydroxyphenylchlorin (mTHPC; 0.03 mg/mL in liposomes)—652 nm light @ 10-20 j/cm2.

Thus, in any of the devices, kits and methods described herein, a non-limiting example use of a photoactive polymerizing polymer is as follows: a first carrier component and a second component can be prepared in any way which, when the two carrier components are combined, combines a photoactive polymerizing polymer and a photinitiator. Alternatively, the first carrier component can include both a photoactive polymerizing polymer and a photinitiator, and the second carrier component can include other materials as detailed elsewhere herein. For example the photoactive polymerizing polymer can be high density collagen (HDC) and the photoinitiator can be riboflavin. Once combined, the photoactive polymerizing polymer and photinitiator are then exposed to an appropriate wavelength of light given the selected photinitiator. For example, if HDC and riboflavin are used, once combined the HDC is photochemically cross-linked by exposure to an appropriate wavelength of light for riboflavin, for example about 458 nm. The resulting photo-chemical cross-linking of the HDC provides a gel scaffold that promotes cell viability and reduces gel contraction. (See, e.g., S. Ibusuki et al., *Photochemically Cross-Linked*

*Collagen Gels as Three-Dimensional Scaffolds for Tissue Engineering*, TISSUE ENGINEERING 13(8): 1995-2001 (2007).

In various aspects, the first predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. The second predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. In one aspect, the first predetermined amount may be about 0.6 cc and the second predetermined amount may be about 1.1 cc.

In any of the devices, kits and methods described herein, the first carrier component, second carrier component, or cell composition may optionally include one or more growth factors, osteostimulative agents, and/or bone morphogenetic proteins, which may be obtained by prior isolation from allogenic bone. Non-limiting examples of such growth factors that may be included into a first or second carrier component or cell composition of the present teachings include a member of the TGF-β superfamily, such as TGF-β1, TGF-β2, TGF-β3, or a bone morphogenetic protein (BMP); a growth differentiation factor; ADMP-1; a fibroblast growth factor (FGF) such as acidic FGF or basic FGF; a member of the hedgehog family of proteins, such as indian hedgehog, sonic hedgehog, or desert hedgehog; a platelet-derived growth factor, an interleukin; a colony-stimulating factor; an activin; a member of the insulin-like growth factor (IGF) family, such as IGF-I or IGF-II; a member of the platelet-derived growth factor (PDGF) family, such as PDGF-AP, PDGF-BB and PDGF-AA; a member of the interleukin (IL) family, such as IL-1, IL-2, IL-3, IL-4, IL-5 or IL-6; or a member of the colony-stimulating factor (CSF) family, such as CSF-1, G-CSF, and GM-CSF. A growth factor may be a growth factor obtained from a tissue source, or can be a recombinant growth factor produced in vitro, in a cell culture, or in a microorganism using standard molecular biology techniques. In some aspects, a growth factor may be a bone morphogenetic protein, such as, in non-limiting example, BMP-1, BMP-2, BMP-3, BMP-4, BMP-5, BMP-6 or BMP-7. Any such growth factors may for example be obtained by prior isolation from bone tissue including allogenic bone tissue. For example, one or more growth factors such as one or more BMPs may be isolated from allogenic bone and incorporated in the first carrier component, second carrier component, or cell composition.

The first carrier component, second carrier component, or cell composition as described herein may comprise, in addition to or instead of a growth factor, nutritional factors, hormones, peptides/proteins, or polysaccharides. Nutritional factors may include, but are not limited to, fatty acids, calcium, dextrose, glucose, glutamine, and vitamins such as vitamin A, B complex vitamins, vitamin C, vitamin D, vitamin E, or vitamin K. Hormones may include, but are not limited to, estrogen, testosterone, growth hormone, and thyroid hormone. Non-limiting examples of peptides or proteins include amino acids, link protein, GHK-copper peptide, BMP-13, BMP-14, PLAB, bone marrow aspirate lysate, and platelet lysate. Non-limiting examples of polysaccharides or monosaccharides includes carbohydrates, such as glucose or polymers thereof, dextran, hyaluronic acid (HyA), oligosaccharides of HyA, heparin, heparan sulfate, N-acetyl-glucosamine, and marine sulfated polysaccharides.

ii. 5-Inlet Injection Preparation Methods

In an aspect, the present disclosure provides a method of preparing a multi-component injection, including obtaining a carrier syringe 104 including at least two barrels with a first carrier component in a first barrel and a second carrier component in a second barrel; coupling a first barrel of the carrier syringe 104 to the first inlet 211 of the injection preparation device 200, and a second barrel of the carrier syringe 104 to the third inlet 213 of the injection preparation device 200; coupling a cell delivery syringe 106 to the second inlet 212 of the injection preparation device 200; coupling a cell transfer syringe 204 to the fifth inlet 215 of the injection preparation device 200; and coupling a carrier delivery syringe 108 to the fourth inlet 214 of the injection preparation device 200. The method may further include transferring the second carrier component from the second barrel of the carrier syringe 104 to the carrier delivery syringe 108 through the second conduit of the injection preparation device. In an aspect, the flow path may be limited through the first conduit of the injection preparation device 200 to between the first inlet 211 and the fifth inlet 215. The method may also include transferring the first carrier component from the first barrel of the carrier syringe 104 to the cell transfer syringe 204 through the first conduit of the injection preparation device 200. A double-barrel plunger rod assembly 118 used with the carrier syringe 104 is configured to transfer a predetermined amount of the first carrier component to the cell transfer syringe 204 and a predetermined amount of the second carrier component to the carrier delivery syringe 108, whereby the first carrier component mixes with the contents of the cell transfer syringe 204. The method may further include limiting the flow path through the first conduit 211 of the injection preparation device 200 to between the fifth inlet 215 and the second inlet 212 and transferring the mixture in the cell transfer syringe 204 to the cell delivery syringe 106. The method may further include decoupling the cell delivery syringe 106 and the carrier delivery syringe 108 from the injection preparation device, where the carrier delivery syringe 108 contains the first second carrier component and the cell delivery syringe 106 contains a first cell/carrier mixture.

In another aspect, the present disclosure provides a method of preparing a multi-component injection, including filling a carrier syringe 104 including at least two barrels with a first carrier component in a first barrel and a second carrier component in a second barrel; coupling the two barrels of the carrier syringe 104 to the first and third inlets 211, 213 of an injection preparation device 200, and coupling the two barrels of the multi-barrel delivery syringe 116 to the second and fourth inlets 212, 214 of the injection preparation device 200, and transferring the first carrier component from the first barrel of the carrier syringe 104 to a first barrel of the delivery syringe 116 through the first conduit of the injection preparation device 200, and the second carrier component from the second barrel of the carrier syringe 104 to a second barrel of the delivery syringe 116 through the second conduit of the injection preparation device 200, where a double-barrel plunger rod assembly 118 used with the carrier syringe 104 may be configured to transfer a predetermined amount of the first carrier component and a predetermined amount of the second carrier component to the delivery syringe 116. The method may further include removing the carrier syringe 104 from the injection preparation device 200; coupling a cell transfer syringe 204 to the injection preparation device 200, where the cell transfer syringe 204 contains a cell composition; transferring the first carrier component from the first barrel of the delivery syringe 116 to the cell transfer syringe 204 though the first conduit, whereby the first carrier component is mixed with the cell composition to form a first cell/carrier mixture; and transferring the first cell/carrier mixture back to the first barrel of the delivery syringe 116 through the first conduit. The method may further include decoupling the delivery syringe 116 from the injection preparation device, where the first barrel of the delivery syringe 116 contains the first cell/carrier mixture and the second barrel of the delivery syringe 116 contains the second carrier component.

The method may further include coupling the delivery syringe 116 to a Y-connector 700 having a stem portion, and ejecting the first cell/carrier mixture from the first barrel of the delivery syringe 116 or the cell delivery syringe 106 and the second carrier component from the second barrel of the delivery syringe 116 or the carrier delivery syringe 108 through the Y-connector 700, whereby the first cell/carrier mixture and the second carrier component are combined in the Y-connector stem portion to form a cell/carrier composition. The Y-connector 700 may be configured to reversibly couple to the cell delivery syringe 106 and to the carrier delivery syringe 108 or the multi-barrel delivery syringe 116, and the Y-connector 700 includes a connector body 702 having a first end and a second end, the first end defining at least two connector inlets for reversibly coupling the Y-connector 700 to the cell delivery syringe 106 and the carrier delivery syringe 108 or to the at least two barrels of the delivery syringe 116; the method further including coupling a dual lumen cannula 704 to the second end of the Y-connector body 702, and coupling a spinal needle to the dual lumen cannula 704.

In an aspect, the method may further include introducing a light source or light conduit, such as an optic fiber or endoscope, to expose photoactivated polymer(s) at or near the end of the dual lumen cannula. In one aspect, the light source and/or light conduit may run the length of the dual cannula. In various aspects, the light source and/or light conduit may be integral or attached to the Y-connector, dual cannula, spinal needle, or delivery syringe. During the repair of the spinal disc annulus it may be desired to use a light polymerizing polymer as a carrier for the delivery of biologic cells or drugs. The advantage in this arrangement is a single carrier component with the mixed in biologic cells or drugs may be sufficient instead of needing a two part carrier that reacts together. In an aspect, the carrier component may be polymerized by light which may be delivered via an integrated fiber optic in or on the spinal needle. This may allow for a rapid hardening of the photoactive polymer so it does not migrate and provide structural support similar to the current properties of the disc annulus. It also may allow for the contouring of the repair by controlled delivery and hardening of the polymer. In another aspect, using a light source with a photoactive polymer may allow for the construction of geometric structures to fit the deflect shape.

In one aspect, the method may include passing the spinal needle through a fiber optic endoscope. The endoscope may allow for illumination and viewing of the defects repair which may allow for the contouring (geometric construction) of the polymerized carrier component with mixed in biologic cells or drugs.

In another aspect, even if the carrier is multi-component and delivered via a multi-barrel delivery syringe, the polymerization rate of the delivered polymer may be 'tuned' via light intensity. In an aspect, the carrier component(s) may be exposed to light to initiate the reaction for polymer polymerization before the carrier component(s) enter the needle and thus would be reacting as it is progressing down the needle to be delivered. This may have the benefit of allowing for a lower profile (outer diameter) spinal needle for delivery.

The methods may further include injecting the cell/carrier composition into a tissue defect. In various aspects, a tissue may be, without limitation, bone, cartilage, tendon tissue, ligament tissue, soft tissue such as vascular tissue, dermal tissue or muscle tissue, neural tissue, or a combination thereof. In some other aspects, a site in need of tissue growth may include tendon tissue, ligament tissue, vascular tissue, dermal tissue, periodontal tissue, intervertebral disc tissue, hyaline cartilage, fibrous cartilage, elastic cartilage, a nerve tunnel or a combination thereof. In another aspect, the tissue may include but is not limited to bone, cartilage or soft tissue. In an aspect, the methods may further include injecting the cell/carrier composition into a degenerated intervertebral disc.

In various configurations, a site in need of tissue growth may include, without limitation, dermis, a rotator cuff tendon, an Achilles tendon, a ligament such as an anterior cruciate ligament (ACL), a posterior cruciate ligament, (PCL), a medial collateral ligament, a lateral collateral ligament or a periodontal figment, a sphincter such as an anal sphincter, a urethral sphincter, an esophageal sphincter or an antral sphincter, herniated tissue such as an abdominal hernia, a Cooper's hernia, a diaphragmatic hernia, an epigastric hernia, a femoral hernia, an incisional hernia, an inguinal hernia, an intervertebral disc hernia, a Littre's hernia, an obturator hernia, a pantaloon hernia, a perineal hernia, a properitoneal hernia, a Richter's hernia, a sciatic hernia, a sliding hernia, a Spigelian hernia or an umbilical hernia, an intervertebral disc nucleus, an intervertebral disc annulus, periosteal tissue, neural tissue such as central nervous system tissue (including spinal cord tissue) and demyelinated neural tissue, peripheral nervous system tissue, a nerve tunnel such as a nerve tunnel traversing bone tissue, a mitral valve, a tricuspid valve, an aortic heart valve, a pulmonary heart valve, vascular tissue comprising a stent, stenotic cardiovascular tissue, cartilage, costal cartilage, meniscus cartilage, epiglottic cartilage, laryngeal cartilage such as arytenoid cartilage, cricoid cartilage, cuneiform cartilage and corniculate cartilage, external ear cartilage, auditory tube cartilage, labral cartilage, articular cartilage, bone, bone defects/voids, muscle, and other soft tissues.

In an aspect, the method may further include monitoring the injection load using an injection load monitoring device 800 reversibly coupled to the cell delivery syringe 106 and the carrier delivery syringe 108 or the multi-barrel delivery syringe 116, the injection load monitoring device 800 may include a mechanical load sensor 802 having an amplifier and an electrical coupling coupled thereto for coupling to a pressure display unit 808; a syringe adapter 804 coupled to the mechanical load sensor 802, the syringe adapter 804 having a first surface configured to engage an outward end portion of a plunger rod of a plunger rod assembly of the delivery syringe 116 or the cell delivery syringe 106 and the carrier delivery syringe 108; and a finger plate 806 coupled to the mechanical load sensor 802.

In an aspect, the mechanical load sensor 802 may be selected from a miniature or subminiature load cell and a piezoresistive force sensor. The mechanical load sensor 802 may be operable for measuring a compression load of up to about 100 lb. In an aspect, the pressure display unit 808 may display a visual alarm, an auditory alarm, or both in response to the pressure applied to the delivery syringe 116. The pressure display unit 800 may be directly coupled to the syringe adapter 804 or finger plate 806. In an aspect, the pressure display unit 808 may be coupled to the mechanical load sensor wirelessly.

In another aspect, the method may include connecting a cell transfer container 502 to a cell storage container 402 by penetrating a needle through the opening covered by a sterile seal of the cell storage container 402. The cell transfer container 502 may engage a syringe barrel, such as the cell transfer syringe through a connector port. In a non-limiting example, the connector port may use a female luer port to reversibly engage a male luer-tipped syringe. The wall of the substantially tubular projection may define an opening therethrough so that the contents of the cell storage container 402 may be visible when the cell transfer container 502 is in use to penetrate the seal by contacting the seal with the hollow needle.

In an aspect, the prepared cell composition may include but is not limited to cells selected from adipocytes, neuronal stem cells, chondrocytes, notochordal cells, chondrogenic cells, mesenchymal stem cells, hematopoietic stem cells, and any pluripotent stem cells including embryonic and induced pluripotent stem cells. The prepared cell composition may include but is not limited to mesenchymal stem cells derived from at least one of bone marrow, adipose tissue, synovium, periosteum, post-partum connective tissue, placenta, cord blood, and umbilical cord.

In various aspects, without limitation, the neuronal stem cells may be used to repair neural tissue, the chrondrocytes or chondrogenic cells may be used to repair cartilage, the notochordal cells may be used to repair intervertebral disc tissue, and the mesenchymal stem cells may be used to repair bone, cartilage, or intervertebral disc tissue.

In an aspect, the carrier syringe 104 may include two barrels and a double-barrel plunger rod assembly 118 configured to transfer a first predetermined amount of a first carrier component and a second predetermined amount of a second carrier component. The double-barrel plunger rod assembly 118 may include a first plunger rod for slidably engaging the first barrel of the carrier syringe and a second plunger rod for slidably engaging the second barrel of the carrier syringe, where the first plunger rod is shorter than the second plunger rod so that the first predetermined amount of the first carrier component is less than the second predetermined amount of the second carrier component.

In an aspect, the first carrier component may be thrombin and the second carrier component may be fibrinogen. Non-limiting examples of the first carrier component include thrombin, fibrinogen, poly(ethylene glycol) (PEG), poly (ethylene oxide) (PEO), poly(vinyl alcohol) (PVA), PEG-polystyrene copolymers (PEG)-(PST), poly(lactic acid), ethylene glycol-lactic acid copolymers, ethylene glycol-lactic acid-caprolactone copolymers, poly(d,l-lactide-co-ε-caprolactone), (poly)-anhydrides, anhydrides, urethanes, polysaccharides, dextran, collagen, hyaluronic acid, diethyl fumarate/poly(propylene fumarate), chitosan, a caprolactone polymer such as polycaprolactone (PCL), polyglycolic acid (PGA), or a copolymer of polylactic acid and polyglycolic acid (PLGA), and combinations thereof. In another aspect, the first carrier component may be a photoactive polymerizing polymer. Non-limiting examples of photoactive polymerizing polymers or monomers include collagen, styrene, N-Vinylpyrrolidone, acrylates, epoxides, urethanes, polyethers, and polyesters. In an aspect, the first carrier component may further include a photoinitiator. In another aspect, the second carrier component may include a photoinitiator. Non-limiting examples of photoinitiators include Diazopyruvate, Rose Bengal, riboflavin, riboflavin 5-monophosphate sodium salt dehydrate, m-tetrahydroxyphenyl-chlorin (mTHPC), benzophenone, xanthones, quinones, benzoin ethers, acetophenones, benzoyl oximes, and acylphosphines.

In various aspects, the first predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. The second predetermined amount may be from about 0.5 cc to about 1.5 cc, from about 0.5 to about 0.7 cc, from about 0.6 cc to about 0.8 cc, from about 0.7 cc to about 0.9 cc, from about 0.8 cc to about 1.0 cc, from about 0.9 cc to about 1.1 cc, from about 1.0 cc to about 1.2 cc, from about 1.1 cc to about 1.3 cc, from about 1.2 cc to about 1.4 cc, and from about 1.3 cc to about 1.5 cc. In one aspect, the first predetermined amount may be about 0.6 cc and the second predetermined amount may be about 1.1 cc.

In any of the devices, kits and methods described herein, the first carrier component, second carrier component, or cell composition may optionally include one or more growth factors, osteostimulative agents, and/or bone morphogenetic proteins, which may be obtained by prior isolation from allogenic bone. Non-limiting examples of such growth factors that may be included into a first or second carrier component or cell composition of the present teachings include a member of the TGF-β superfamily, such as TGF-β1, TGF-β2, TGF-β3, or a bone morphogenetic protein (BMP); a growth differentiation factor; ADMP-1; a fibroblast growth factor (FGF) such as acidic FGF or basic FGF; a member of the hedgehog family of proteins, such as indian hedgehog, sonic hedgehog, or desert hedgehog; a platelet-derived growth factor, an interleukin; a colony-stimulating factor; an activin; a member of the insulin-like growth factor (IGF) family, such as IGF-I or IGF-II; a member of the platelet-derived growth factor (PDGF) family, such as PDGF-AP, PDGF-BB and PDGF-AA; a member of the interleukin (IL) family, such as IL-1, IL-2, IL-3, IL-4, IL-5 or IL-6; or a member of the colony-stimulating factor (CSF) family, such as CSF-1, G-CSF, and GM-CSF. A growth factor may be a growth factor obtained from a tissue source, or can be a recombinant growth factor produced in vitro, in a cell culture, or in a microorganism using standard molecular biology techniques. In some aspects, a growth factor may be a bone morphogenetic protein, such as, in non-limiting example, BMP-1, BMP-2, BMP-3, BMP-4, BMP-5, BMP-6 or BMP-7. Any such growth factors may for example be obtained by prior isolation from bone tissue including allogenic bone tissue. For example, one or more growth factors such as one or more BMPs may be isolated from allogenic bone and incorporated in the first carrier component, second carrier component, or cell composition.

The first carrier component, second carrier component, or cell composition as described herein may comprise, in addition to or instead of a growth factor, nutritional factors, hormones, peptides/proteins, or polysaccharides. Nutritional factors may include, but are not limited to, fatty acids, calcium, dextrose, glucose, glutamine, and vitamins such as vitamin A, B complex vitamins, vitamin C, vitamin D, vitamin E, or vitamin K. Hormones may include, but are not limited to, estrogen, testosterone, growth hormone, and thyroid hormone. Non-limiting examples of peptides or proteins include amino acids, link protein, GHK-copper peptide, BMP-13, BMP-14, PLAB, bone marrow aspirate lysate, and platelet lysate. Non-limiting examples of polysaccharides or monosaccharides includes carbohydrates, such as glucose or polymers thereof, dextran, hyaluronic acid (HyA), oligosaccharides of HyA, heparin, heparan sulfate, N-acetyl-glucosamine, and marine sulfated polysaccharides.

Example 1: Photo-Cross-Linked Carrier

To demonstrate the use of a photoactive polymerizing polymer, the following example was performed. Acid soluble Type 1 collagen (pH 1.0) sourced from bovine skin or tendon (1-40 mg/mL) was used to prepare hydrogel carrier for cell delivery. A collagen solution was neutralized to pH 7.4 using 2.2% sodium bicarbonate/0.8M sodium hydroxide. A photo-initiator (riboflavin5-mono-phosphate sodium salt [Sigma-Aldrich]) was added to the collagen solution to yield a final concentration of 0.5 mM. A chondrocyte suspension (1 million per mL human juvenile articular chondrocytes) was then mixed 1:1 with the collagen solution containing 0.5 mM riboflavin, pipetted at increasing volume into 96 well plates (50-400 microliters) and exposed to blue light for 40 seconds. Plates were then incubated at 37 C for 24 and 48 hrs, at which time the metabolic activity was assessed using PrestoBlue, according to manufacturer's instructions (Life Technologies). Two additional plates were set up in the absence of hydrogel to demonstrate that photo-crosslinking has a negligible effect on chondrocyte viability and measured metabolic activity 24 and 48 hrs post-plating.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

What is claimed is:

1. An injection preparation device comprising:
a body adapted to reversibly couple to a cell transfer syringe, a carrier delivery syringe, a cell delivery syringe, and a multi-barrel carrier syringe, the body comprising:
a first conduit having a first inlet configured to reversibly couple to a first barrel of the multi-barrel carrier syringe, a second inlet configured to reversibly couple to a barrel of the cell delivery syringe, and a fifth inlet configured to reversibly couple to a barrel of the cell transfer syringe, wherein the first, second, and fifth inlets communicate through the first conduit, forming a first flow path; and
a second conduit having a third inlet configured to reversibly couple to a second barrel of the multi-barrel carrier syringe and a fourth inlet configured to reversibly couple to a barrel of the carrier delivery syringe, wherein the third inlet and the fourth inlet communicate through the second conduit, forming a second flow path;
wherein the first flow path is limited to between the first, second, and fifth inlets, and wherein the second flow path is limited to between the third and fourth inlets.

2. The injection preparation device of claim 1, wherein the first conduit comprises a two-way valve configured to limit the first flow path to one of: i) between the first and second inlets, and ii) between the second and fifth inlets.

3. The injection preparation device of claim 1, wherein the third inlet defined by the second conduit comprises a one-way valve.

4. The injection preparation device of claim 1 further comprising a double-barrel carrier syringe reversibly coupled to the first inlet and third inlet, a cell delivery syringe reversibly coupled to the second inlet and a carrier delivery syringe reversibly coupled to the fourth inlet, and a cell transfer syringe reversibly coupled to the fifth inlet.

5. The injection preparation device of claim 4, wherein the double-barrel carrier syringe comprises a double-barrel plunger rod assembly comprising a first plunger rod for slidably engaging a first barrel of the double-barrel carrier syringe and a second plunger rod for slidably engaging a second barrel of the double-barrel carrier syringe.

6. The injection preparation device of claim 5, wherein the first plunger rod is shorter than the second plunger rod.

7. The injection preparation device of claim 4, wherein the carrier delivery syringe and the cell delivery syringe are configured to engage an injection load monitoring device comprising:
a mechanical load sensor having an amplifier and an electrical coupling coupled thereto for coupling to a pressure display unit; and
a syringe adapter coupled to the mechanical load sensor, and a finger plate having a first surface configured to engage an outward end portion of a first plunger rod slidably engaging the barrel of the cell delivery syringe and an outward end portion of a second plunger rod slidably engaging the barrel of the carrier delivery syringe.

8. The injection preparation device of claim 7, wherein the mechanical load sensor is selected from the group consisting of a miniature or subminiature load cell and a piezoresistive mechanical load sensor.

9. The injection preparation device of claim 7, wherein the mechanical load sensor is operable for measuring a compression load of up to about 100 lb.

10. An injection kit comprising:
the injection preparation device of claim 1; and
at least one each of a cell transfer syringe, a carrier delivery syringe, a cell delivery syringe, and a multi-barrel carrier syringe.

11. The injection kit of claim 10, further comprising:
a Y-connector configured to reversibly couple to the cell delivery syringe and the carrier delivery syringe, the Y-connector comprising:
a connector body having a first end and a second end, the first end defining at least two connector inlets for reversibly coupling the Y-connector to a barrel of the cell delivery syringe and a barrel of the carrier delivery syringe;
a dual lumen cannula coupled to the second end of the connector body;
a spinal needle coupled to the dual lumen cannula; and
an injection load monitoring device configured to reversibly couple to the cell delivery syringe and the carrier delivery syringe, wherein the injection load monitoring device comprises a mechanical load sensor having an amplifier and an electrical coupling coupled thereto for coupling to a pressure display unit.

12. The injection kit of claim 10, further comprising an amount of a prepared cell composition, wherein the prepared cell composition comprises cells selected from the group consisting of neuronal stem cells, chondrocytes, notochordal cells, chondrogenic cells, mesenchymal stem cells, hematopoietic stem cells, pluripotent stem cells, and induced pluripotent stem cells.

13. The injection kit of claim 10, wherein the multi-barrel carrier syringe is a double-barrel carrier syringe comprising a double-barrel plunger rod assembly configured to transfer a first predetermined amount of a first carrier component and a second predetermined amount of a second carrier component, wherein the double-barrel plunger rod assembly comprises a first plunger rod for slidably engaging the first barrel of the double-barrel carrier syringe and a second plunger rod for slidably engaging the second barrel of the double-barrel carrier syringe.

14. The injection kit of claim 13, wherein the first carrier component is thrombin and the second carrier component is fibrinogen.

15. The injection kit of claim 13, wherein the first carrier component and the second carrier component combine to form a carrier selected from the group consisting of: poly(ethylene glycol) (PEG), poly(ethylene oxide) (PEO), poly(vinyl alcohol) (PVA), PEG-polystyrene copolymers (PEG)-(PST), poly(lactic acid), ethylene glycol-lactic acid copolymers, ethylene glycol-lactic acid-caprolactone copolymers, poly(d,l-lactide-co-ε-caprolactone), (poly)-anhydrides, anhydrides, urethanes, polysaccharides, dextran, collagen, hyaluronic acid, diethyl fumarate/poly(propylene fumarate), chitosan, fibrin, and combinations thereof.

\* \* \* \* \*